United States Patent
Ni et al.

(10) Patent No.: US 11,511,117 B2
(45) Date of Patent: Nov. 29, 2022

(54) METHOD AND SYSTEM FOR APPLYING STIMULATION IN TREATING SLEEP DISORDERED BREATHING

(71) Applicant: INSPIRE MEDICAL SYSTEMS, INC., Golden Valley, MN (US)

(72) Inventors: Quan Ni, Golden Valley, MN (US); Mark A. Christopherson, Golden Valley, MN (US); John Rondoni, Golden Valley, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 45 days.

(21) Appl. No.: 16/813,234

(22) Filed: Mar. 9, 2020

(65) Prior Publication Data
US 2020/0206513 A1 Jul. 2, 2020

Related U.S. Application Data

(63) Continuation of application No. 15/866,164, filed on Jan. 9, 2018, now Pat. No. 10,583,297, which is a
(Continued)

(51) Int. Cl.
*A61N 1/36* (2006.01)
*A61N 1/05* (2006.01)
(Continued)

(52) U.S. Cl.
CPC ............ *A61N 1/36139* (2013.01); *A61B 5/08* (2013.01); *A61B 5/0826* (2013.01);
(Continued)

(58) Field of Classification Search
CPC .............. A61N 1/36139; A61N 1/0556; A61N 1/3611; A61N 1/36128; A61N 1/36135;
(Continued)

(56) References Cited

U.S. PATENT DOCUMENTS

| 4,379,462 A | 4/1983 | Borkan et al. |
| 4,567,892 A | 2/1986 | Plicchi et al. |

(Continued)

FOREIGN PATENT DOCUMENTS

| JP | H11514557 | 12/1992 |
| JP | 2010502276 | 1/2010 |

(Continued)

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).

(Continued)

*Primary Examiner* — Paula J Stice
(74) *Attorney, Agent, or Firm* — Dicke, Billig & Czaja, PLLC

(57) ABSTRACT

A stimulation protocol determination system includes an input module and a selector module. The input module is provided to receive an indication of an upper airway flow limitation via sensed respiratory effort information. The selection module is provided to automatically select, based on the indicated upper airway flow limitation, a stimulation protocol.

10 Claims, 13 Drawing Sheets

Related U.S. Application Data continuation of application No. 14/238,359, filed as application No. PCT/US2012/050615 on Aug. 13, 2012, now abandoned.

(60) Provisional application No. 61/522,426, filed on Aug. 11, 2011.

(51) Int. Cl.
| | |
|---|---|
| *A61B 5/08* | (2006.01) |
| *A61B 5/00* | (2006.01) |
| *A61B 5/053* | (2021.01) |
| *A61B 5/085* | (2006.01) |
| *A61B 5/087* | (2006.01) |
| *A61B 5/318* | (2021.01) |

(52) U.S. Cl.
CPC ............ *A61B 5/4836* (2013.01); *A61B 5/686* (2013.01); *A61N 1/0556* (2013.01); *A61N 1/3611* (2013.01); *A61B 5/053* (2013.01); *A61B 5/085* (2013.01); *A61B 5/087* (2013.01); *A61B 5/318* (2021.01); *A61B 2562/0247* (2013.01)

(58) Field of Classification Search
CPC ......... A61B 5/686; A61B 5/08; A61B 5/4836; A61B 5/0826; A61B 5/318; A61B 5/05; A61B 5/087; A61B 5/0871; A61B 5/085; A61B 2562/0247
See application file for complete search history.

(56) References Cited

U.S. PATENT DOCUMENTS

| | | |
|---|---|---|
| 4,630,614 A | 12/1986 | Atlas |
| 4,813,431 A | 3/1989 | Brown |
| 4,830,008 A | 5/1989 | Meer |
| 5,133,354 A | 7/1992 | Kallok |
| 5,134,995 A | 8/1992 | Gruenke et al. |
| 5,148,802 A | 9/1992 | Sanders et al. |
| 5,158,080 A | 10/1992 | Kallok |
| 5,167,229 A | 12/1992 | Peckham et al. |
| 5,174,287 A | 12/1992 | Kallok et al. |
| 5,178,156 A | 1/1993 | Takishima et al. |
| 5,203,343 A | 4/1993 | Axe et al. |
| 5,211,173 A | 5/1993 | Kallok et al. |
| 5,215,082 A | 6/1993 | Kallok et al. |
| 5,233,983 A | 8/1993 | Markowitz |
| 5,239,995 A | 8/1993 | Estes et al. |
| 5,245,995 A | 9/1993 | Sullivan et al. |
| 5,265,624 A | 11/1993 | Bowman |
| 5,281,219 A | 1/1994 | Kallok |
| 5,300,094 A | 4/1994 | Kallok et al. |
| 5,335,657 A | 8/1994 | Terry, Jr. et al. |
| 5,344,438 A | 9/1994 | Testerman et al. |
| 5,351,394 A | 10/1994 | Weinberg |
| 5,385,144 A | 1/1995 | Yamanishi et al. |
| 5,388,578 A | 2/1995 | Yomtov et al. |
| 5,398,682 A | 3/1995 | Lynn |
| 5,458,137 A | 10/1995 | Axe et al. |
| 5,483,969 A | 1/1996 | Testerman et al. |
| 5,485,851 A | 1/1996 | Erickson |
| 5,522,862 A | 6/1996 | Testerman et al. |
| 5,524,632 A | 6/1996 | Stein et al. |
| 5,540,731 A | 7/1996 | Testerman |
| 5,540,732 A | 7/1996 | Testerman |
| 5,540,733 A | 7/1996 | Testerman et al. |
| 5,540,734 A | 7/1996 | Zabara |
| 5,546,952 A | 8/1996 | Erickson |
| 5,549,655 A | 8/1996 | Erickson |
| 5,588,439 A | 12/1996 | Hollub |
| 5,591,216 A | 1/1997 | Testerman et al. |
| 5,605,151 A | 2/1997 | Lynn |
| 5,645,053 A | 7/1997 | Remmers et al. |
| 5,671,733 A | 9/1997 | Raviv et al. |
| 5,797,852 A | 8/1998 | Karakasoglu et al. |
| 5,823,187 A | 10/1998 | Estes et al. |
| 5,843,135 A | 12/1998 | Weijand et al. |
| 5,895,360 A | 4/1999 | Christopherson et al. |
| 5,904,141 A | 5/1999 | Estes et al. |
| 5,919,221 A | 7/1999 | Miesel |
| 5,944,680 A | 8/1999 | Christopherson et al. |
| 5,999,846 A | 12/1999 | Pardey et al. |
| 6,015,389 A | 1/2000 | Brown |
| 6,021,352 A | 2/2000 | Christopherson et al. |
| 6,025,624 A | 2/2000 | Figura |
| 6,041,780 A | 3/2000 | Richard et al. |
| 6,099,479 A | 8/2000 | Christopherson et al. |
| 6,120,441 A | 9/2000 | Griebel |
| 6,125,290 A | 9/2000 | Miesel |
| 6,125,291 A | 9/2000 | Miesel et al. |
| 6,126,611 A | 10/2000 | Bourgeouis et al. |
| 6,132,384 A | 10/2000 | Christopherson et al. |
| 6,134,459 A | 10/2000 | Roberts et al. |
| 6,144,866 A | 11/2000 | Miesel et al. |
| 6,175,767 B1 | 1/2001 | Doyle, Sr. |
| 6,181,961 B1 | 1/2001 | Prass |
| 6,198,952 B1 | 3/2001 | Miesel |
| 6,223,064 B1 | 4/2001 | Lynn et al. |
| 6,240,316 B1 | 5/2001 | Richmond et al. |
| 6,248,080 B1 | 6/2001 | Miesel et al. |
| 6,249,703 B1 | 6/2001 | Stanton et al. |
| 6,251,126 B1 | 6/2001 | Ottenhoff et al. |
| 6,269,269 B1 | 7/2001 | Ottenhoff et al. |
| 6,307,481 B1 | 10/2001 | Lehrman et al. |
| 6,309,350 B1 | 10/2001 | Van Tassel et al. |
| 6,314,324 B1 | 11/2001 | Lattner et al. |
| 6,342,039 B1 | 1/2002 | Lynn et al. |
| 6,345,202 B2 | 2/2002 | Richmond et al. |
| 6,361,494 B1 | 3/2002 | Lindenthaler |
| 6,393,325 B1 | 5/2002 | Mann et al. |
| 6,449,507 B1 | 9/2002 | Hill et al. |
| 6,450,957 B1 | 9/2002 | Yoshimi et al. |
| 6,456,866 B1 | 9/2002 | Tyler et al. |
| 6,522,928 B2 | 2/2003 | Whitehurst et al. |
| 6,532,388 B1 | 3/2003 | Hill et al. |
| 6,572,543 B1 | 6/2003 | Christopherson et al. |
| 6,574,507 B1 | 6/2003 | Bonnet |
| 6,587,725 B1 | 7/2003 | Durand et al. |
| 6,609,016 B1 | 8/2003 | Lynn |
| 6,609,032 B1 | 8/2003 | Woods et al. |
| 6,629,527 B1 | 10/2003 | Estes et al. |
| 6,641,542 B2 | 11/2003 | Cho et al. |
| 6,645,143 B2 | 11/2003 | Van Tassel et al. |
| 6,647,289 B2 | 11/2003 | Prutchi |
| 6,651,652 B1 | 11/2003 | Ward |
| 6,654,634 B1 | 11/2003 | Prass |
| 6,665,560 B2 | 12/2003 | Becker et al. |
| 6,666,830 B1 | 12/2003 | Lehrman et al. |
| 6,689,068 B2 | 2/2004 | Hale et al. |
| 6,703,939 B2 | 3/2004 | Lehrman et al. |
| 6,718,208 B2 | 4/2004 | Hill et al. |
| 6,719,708 B1 | 4/2004 | Jansen |
| 6,731,976 B2 | 5/2004 | Penn et al. |
| 6,731,984 B2 | 5/2004 | Cho et al. |
| 6,735,471 B2 | 5/2004 | Hill et al. |
| 6,752,765 B1 | 6/2004 | Jensen et al. |
| 6,770,022 B2 | 8/2004 | Mechlenburg et al. |
| 6,773,404 B2 | 8/2004 | Poezevera et al. |
| 6,805,667 B2 | 10/2004 | Christopherson et al. |
| 6,811,538 B2 | 11/2004 | Westbrook et al. |
| 6,842,647 B1 | 1/2005 | Griffith et al. |
| 6,881,192 B1 | 4/2005 | Park |
| 6,890,306 B2 | 5/2005 | Poezevera |
| 6,893,405 B2 | 5/2005 | Kumar et al. |
| 6,904,320 B2 | 6/2005 | Park et al. |
| 6,907,293 B2 | 6/2005 | Grill et al. |
| 6,928,324 B2 | 8/2005 | Park et al. |
| 6,935,335 B1 | 8/2005 | Lehrman et al. |
| 6,936,011 B2 | 8/2005 | Sheldon |
| 6,964,641 B2 | 11/2005 | Cho et al. |
| 6,978,171 B2 | 12/2005 | Goetz et al. |
| 6,988,498 B2 | 1/2006 | Berthon-Jones et al. |

(56) References Cited

U.S. PATENT DOCUMENTS

| | | |
|---|---|---|
| 7,025,730 B2 | 4/2006 | Cho et al. |
| 7,041,049 B1 | 5/2006 | Raniere |
| 7,054,692 B1 | 5/2006 | Whitehurst et al. |
| 7,077,810 B2 | 7/2006 | Lange et al. |
| 7,081,095 B2 | 7/2006 | Lynn et al. |
| 7,082,331 B1 | 7/2006 | Park et al. |
| 7,082,336 B2 | 7/2006 | Ransbury et al. |
| 7,087,053 B2 | 8/2006 | Vanney |
| 7,117,036 B2 | 10/2006 | Florio |
| 7,128,717 B1 | 10/2006 | Thach et al. |
| 7,145,461 B2 | 12/2006 | Lehrman et al. |
| 7,149,573 B2 | 12/2006 | Wang |
| 7,155,278 B2 | 12/2006 | King et al. |
| 7,160,252 B2 | 1/2007 | Cho et al. |
| 7,160,255 B2 | 1/2007 | Saadat |
| 7,167,743 B2 | 1/2007 | Heruth et al. |
| 7,174,215 B2 | 2/2007 | Bradley |
| 7,186,220 B2 | 3/2007 | Stahmann et al. |
| 7,187,978 B2 | 3/2007 | Malek et al. |
| 7,189,204 B2 | 3/2007 | Ni et al. |
| 7,195,594 B2 | 3/2007 | Eigler et al. |
| 7,200,440 B2 | 4/2007 | Kim et al. |
| 7,206,635 B2 | 4/2007 | Cho et al. |
| 7,212,862 B2 | 5/2007 | Park et al. |
| 7,214,197 B2 | 5/2007 | Prass |
| 7,252,640 B2 | 8/2007 | Ni et al. |
| 7,269,457 B2 | 9/2007 | Shafer et al. |
| 7,269,459 B1 | 9/2007 | Koh |
| 7,277,749 B2 | 10/2007 | Gordon et al. |
| 7,330,760 B2 | 2/2008 | Heruth et al. |
| 7,336,996 B2 | 2/2008 | Hartley et al. |
| 7,340,302 B1 | 3/2008 | Falkenberg |
| 7,351,208 B2 | 4/2008 | Brodnick et al. |
| 7,366,572 B2 | 4/2008 | Heruth et al. |
| 7,371,220 B1 | 5/2008 | Koh et al. |
| 7,387,608 B2 | 6/2008 | Dunlop et al. |
| 7,395,113 B2 | 7/2008 | Heruth et al. |
| 7,396,333 B2 | 7/2008 | Stahmann et al. |
| 7,398,115 B2 | 7/2008 | Lynn |
| 7,422,015 B2 | 9/2008 | Delisle et al. |
| 7,438,686 B2 | 10/2008 | Cho et al. |
| 7,447,545 B2 | 11/2008 | Heruth et al. |
| 7,454,250 B1 | 11/2008 | Bjorling et al. |
| 7,453,928 B2 | 12/2008 | Lee et al. |
| 7,468,040 B2 | 12/2008 | Hartley et al. |
| 7,469,697 B2 | 12/2008 | Lee et al. |
| 7,473,227 B2 | 1/2009 | Hsu et al. |
| 7,491,181 B2 | 2/2009 | Heruth et al. |
| 7,509,164 B2 | 3/2009 | Jensen |
| 7,510,531 B2 | 3/2009 | Lee et al. |
| 7,526,341 B2 | 4/2009 | Goetz et al. |
| 7,542,803 B2 | 6/2009 | Heruth et al. |
| 7,572,225 B2 | 8/2009 | Stahmann et al. |
| 7,590,455 B2 | 9/2009 | Heruth et al. |
| 7,591,265 B2 | 9/2009 | Lee et al. |
| 7,596,413 B2 | 9/2009 | Libbus et al. |
| 7,603,170 B2 | 10/2009 | Hatlestad et al. |
| 7,610,094 B2 | 10/2009 | Stahmann et al. |
| 7,634,315 B2 | 12/2009 | Cholette |
| 7,644,714 B2 | 1/2010 | Atkinson et al. |
| 7,662,105 B2 | 2/2010 | Hatlestad |
| 7,672,728 B2 | 3/2010 | Libbus et al. |
| 7,678,061 B2 | 3/2010 | Lee et al. |
| 7,680,538 B2 | 3/2010 | Durand et al. |
| 7,702,385 B2 | 4/2010 | Moffitt et al. |
| 7,717,848 B2 | 5/2010 | Heruth et al. |
| 7,720,541 B2 | 5/2010 | Stahmann et al. |
| 7,725,195 B2 | 5/2010 | Lima et al. |
| 7,734,340 B2 | 6/2010 | De Ridder |
| 7,734,350 B2 | 6/2010 | Dubnov et al. |
| 7,742,819 B2 | 6/2010 | Moffitt |
| 7,747,323 B2 | 6/2010 | Libbus et al. |
| 7,751,880 B1 | 7/2010 | Cholette |
| 7,775,993 B2 | 8/2010 | Heruth et al. |
| 7,783,353 B2 | 8/2010 | Libbus et al. |
| 7,792,583 B2 | 9/2010 | Miesel et al. |
| 7,809,442 B2 | 10/2010 | Bolea et al. |
| 7,818,063 B2 | 10/2010 | Wallace et al. |
| 7,853,322 B2 | 12/2010 | Bourget et al. |
| 7,881,798 B2 | 2/2011 | Miesel et al. |
| 7,908,013 B2 | 3/2011 | Miesel et al. |
| 7,917,230 B2 | 3/2011 | Bly |
| 7,942,822 B1 | 5/2011 | Koh |
| 7,957,797 B2 | 6/2011 | Bourget et al. |
| 7,957,809 B2 | 6/2011 | Bourget et al. |
| 7,979,128 B2 | 7/2011 | Tehrani et al. |
| 8,016,776 B2 | 9/2011 | Bourget et al. |
| 8,021,299 B2 | 9/2011 | Miesel et al. |
| 8,150,531 B2 | 4/2012 | Skelton |
| 8,160,711 B2 | 4/2012 | Tehrani et al. |
| 8,175,720 B2 | 5/2012 | Skelton et al. |
| 8,280,513 B2 | 10/2012 | Tehrani et al. |
| 2001/0010010 A1 | 7/2001 | Richmond et al. |
| 2002/0010495 A1 | 1/2002 | Freed et al. |
| 2002/0049479 A1 | 4/2002 | Pitts |
| 2002/0156507 A1 | 10/2002 | Lindenthaler |
| 2003/0093128 A1 | 5/2003 | Freed et al. |
| 2003/0114905 A1 | 6/2003 | Kuzma |
| 2003/0224895 A1 | 6/2003 | Gordon et al. |
| 2003/0163059 A1 | 8/2003 | Poezevera et al. |
| 2003/0195571 A1 | 10/2003 | Burnes et al. |
| 2003/0216789 A1 | 11/2003 | Deem et al. |
| 2004/0015204 A1 | 1/2004 | Whitehurst et al. |
| 2004/0073272 A1 | 4/2004 | Knudson et al. |
| 2004/0111139 A1 | 6/2004 | McCreery |
| 2004/0215288 A1 | 10/2004 | Lee et al. |
| 2004/0230278 A1 | 11/2004 | Dahl et al. |
| 2004/0254612 A1* | 12/2004 | Ezra ............... A61N 1/3621 607/5 |
| 2005/0004628 A1 | 1/2005 | Goetz et al. |
| 2005/0010265 A1 | 1/2005 | Baru Fassio et al. |
| 2005/0042589 A1 | 2/2005 | Hatlestad et al. |
| 2005/0043765 A1 | 2/2005 | Williams et al. |
| 2005/0043772 A1 | 2/2005 | Stahmann et al. |
| 2005/0074741 A1 | 4/2005 | Lee et al. |
| 2005/0076908 A1 | 4/2005 | Lee et al. |
| 2005/0080348 A1 | 4/2005 | Stahmann et al. |
| 2005/0080461 A1 | 4/2005 | Stahmann et al. |
| 2005/0081847 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0101833 A1 | 5/2005 | Hsu et al. |
| 2005/0113710 A1 | 5/2005 | Stahmann et al. |
| 2005/0115561 A1 | 6/2005 | Stahmann et al. |
| 2005/0145246 A1 | 7/2005 | Hartley et al. |
| 2005/0165457 A1 | 7/2005 | Benser et al. |
| 2005/0182457 A1 | 8/2005 | Thrope et al. |
| 2005/0209513 A1 | 9/2005 | Heruth et al. |
| 2005/0209643 A1 | 9/2005 | Heruth et al. |
| 2005/0222503 A1 | 10/2005 | Dunlop et al. |
| 2005/0234523 A1 | 10/2005 | Levin et al. |
| 2005/0251216 A1 | 11/2005 | Hill et al. |
| 2005/0261747 A1 | 11/2005 | Schuler et al. |
| 2005/0267380 A1 | 12/2005 | Poezevera |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0052836 A1 | 3/2006 | Kim et al. |
| 2006/0058852 A1 | 3/2006 | Koh et al. |
| 2006/0064029 A1 | 3/2006 | Arad (Abboud) |
| 2006/0079802 A1 | 4/2006 | Jensen et al. |
| 2006/0095088 A1 | 5/2006 | De Ridder |
| 2006/0103407 A1 | 5/2006 | Kakizawa et al. |
| 2006/0135886 A1 | 6/2006 | Lippert et al. |
| 2006/0142815 A1 | 6/2006 | Tehrani et al. |
| 2006/0155341 A1* | 7/2006 | Tehrani ............... A61B 5/08 607/42 |
| 2006/0212096 A1 | 9/2006 | Stevenson |
| 2006/0224209 A1 | 10/2006 | Meyer |
| 2006/0224211 A1* | 10/2006 | Durand ............ A61N 1/3601 607/42 |

(56) References Cited

U.S. PATENT DOCUMENTS

| | | |
|---|---|---|
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271137 A1 | 11/2006 | Stanton-Hicks |
| 2006/0276701 A1 | 12/2006 | Ray |
| 2006/0293720 A1 | 12/2006 | DiLorenzo |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/0150022 A1 | 6/2007 | Ujhazy et al. |
| 2007/0233204 A1 | 10/2007 | Lima et al. |
| 2007/0255379 A1 | 11/2007 | Williams et al. |
| 2008/0009685 A1 | 1/2008 | Kim et al. |
| 2008/0039904 A1 | 2/2008 | Bulkes et al. |
| 2008/0046055 A1 | 2/2008 | Durand et al. |
| 2008/0064977 A1 | 3/2008 | Kelleher et al. |
| 2008/0103407 A1* | 5/2008 | Bolea ............ A61N 1/37229 607/42 |
| 2008/0103545 A1 | 5/2008 | Bolea et al. |
| 2008/0103570 A1 | 5/2008 | Gerber |
| 2008/0109046 A1 | 5/2008 | Lima et al. |
| 2008/0109048 A1 | 5/2008 | Moffitt |
| 2008/0132802 A1 | 6/2008 | Ni et al. |
| 2008/0294060 A1 | 11/2008 | Haro et al. |
| 2009/0024047 A1 | 1/2009 | Shipley et al. |
| 2009/0062882 A1 | 3/2009 | Zhang et al. |
| 2009/0112116 A1 | 4/2009 | Lee et al. |
| 2009/0118787 A1 | 5/2009 | Moffitt et al. |
| 2009/0234427 A1 | 9/2009 | Chinn et al. |
| 2009/0287279 A1 | 11/2009 | Parramon et al. |
| 2009/0308395 A1 | 12/2009 | Lee et al. |
| 2009/0326408 A1 | 12/2009 | Moon |
| 2010/0010566 A1 | 1/2010 | Thacker et al. |
| 2010/0016749 A1 | 1/2010 | Atsma et al. |
| 2010/0094379 A1 | 4/2010 | Meadows |
| 2010/0125310 A1 | 5/2010 | Wilson et al. |
| 2010/0125314 A1 | 5/2010 | Bradley et al. |
| 2010/0125315 A1 | 5/2010 | Parramon et al. |
| 2010/0137931 A1 | 6/2010 | Hopper et al. |
| 2010/0152553 A1 | 6/2010 | Ujhazy et al. |
| 2010/0174341 A1 | 7/2010 | Bolea et al. |
| 2010/0198103 A1 | 8/2010 | Meadows et al. |
| 2010/0198289 A1* | 8/2010 | Kameli ............ A61B 5/4094 607/14 |
| 2010/0228133 A1 | 9/2010 | Averina et al. |
| 2010/0228310 A1 | 9/2010 | Shuros et al. |
| 2010/0228317 A1 | 9/2010 | Libbus et al. |
| 2010/0241195 A1 | 9/2010 | Meadows et al. |
| 2010/0262210 A1 | 10/2010 | Parramon et al. |
| 2011/0093036 A1 | 4/2011 | Mashiach |
| 2011/0112601 A1 | 5/2011 | Meadows et al. |
| 2011/0152706 A1 | 6/2011 | Christopherson et al. |
| 2011/0152965 A1 | 6/2011 | Mashiach et al. |
| 2011/0160794 A1 | 6/2011 | Bolea et al. |
| 2011/0264164 A1 | 10/2011 | Christopherson et al. |

FOREIGN PATENT DOCUMENTS

| | | |
|---|---|---|
| JP | 2011520526 | 7/2011 |
| WO | 199750049 | 12/1997 |
| WO | 2006047264 | 5/2006 |
| WO | 2006057734 | 6/2006 |
| WO | 2006102591 | 9/2006 |
| WO | 2007068284 | 6/2007 |
| WO | 2008048471 | 4/2008 |
| WO | 2009048580 | 4/2009 |
| WO | 2009048581 | 4/2009 |
| WO | 2009135138 | 11/2009 |
| WO | 2009135140 | 11/2009 |
| WO | 2009140636 | 11/2009 |
| WO | 2010039853 | 4/2010 |
| WO | 2010057286 | 5/2010 |
| WO | 2010059839 | 5/2010 |
| WO | 2010117810 | 10/2010 |

OTHER PUBLICATIONS

Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.

Naples Article—Gregory G. Naples et al., "A Spiral Nerve Cuff Electrode for Peripheral Nerve Stimulation," 8088 IEEE Transactions on Biomedical Engineering, 35. Nov. 1988, No. 11, New York, NY, pp. 905-915.

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol HeadAnd Neck Surg., vol. 127, Oct. 2001, pp. 1216-1223. Copyright 2001 American Medical Association. (8 pages).

Park, "Preoperative Percutaneous Cranial Nerve Mapping in Head and Neck Surgery," Arch Facial Plast Surg/vol. 5, Jan./Feb. 2003, www.archfacial.compp. 86-91.

Stanescu et al., "Expiratory flow limitation during sleep in heavy snorers", European Respiratory Journal, 1996, pp. 2116-2121.

* cited by examiner

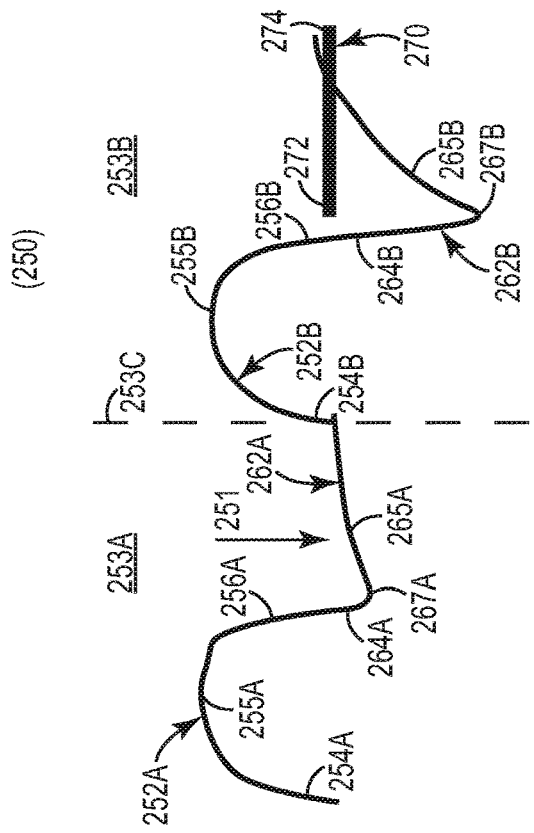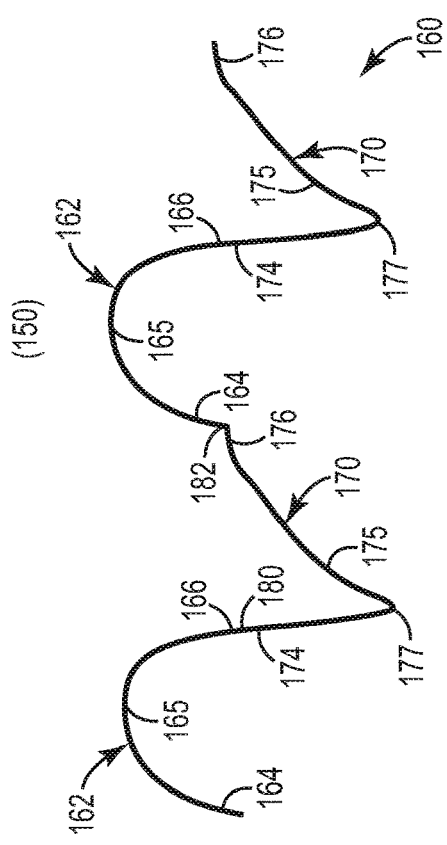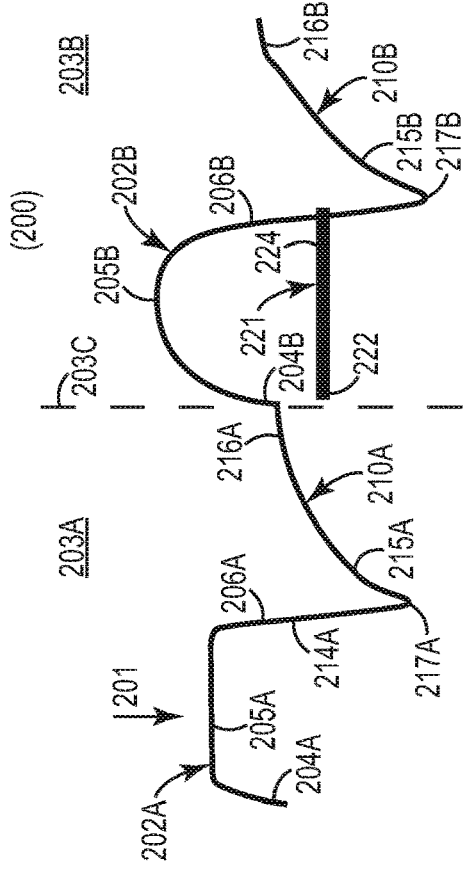

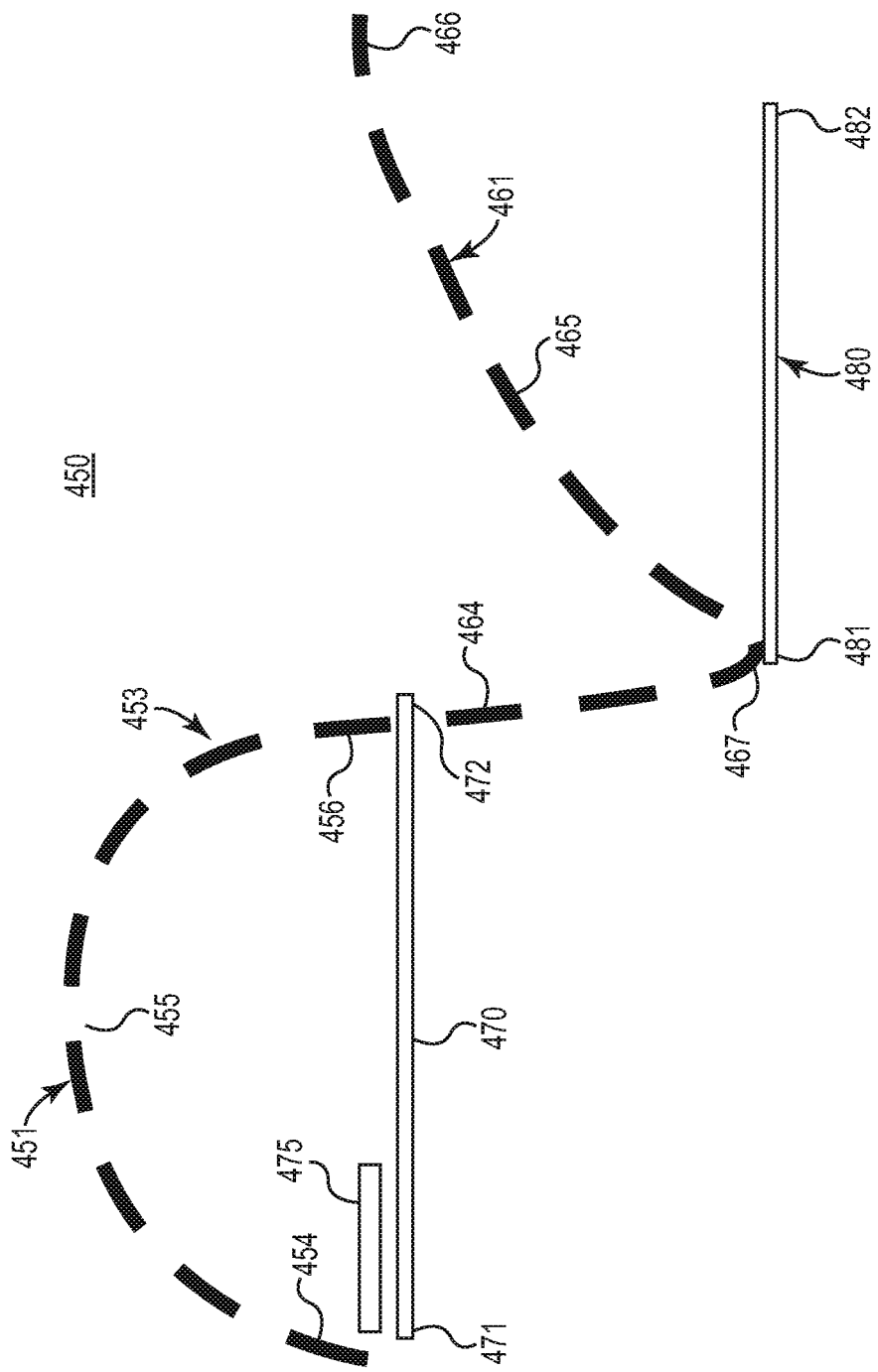

METHOD AND SYSTEM FOR APPLYING STIMULATION IN TREATING SLEEP DISORDERED BREATHING

CROSS-REFERENCE TO RELATED APPLICATION

This application is a continuation of U.S. patent application Ser. No. 15/866,164, entitled "Method and System for Applying Stimulation in Treating Sleep Disordered Breathing" filed Jan. 9, 2018, which is a continuation of U.S. patent application Ser. No. 14/238,359, entitled "Nerve Stimulation Protocol Determination" filed Oct. 14, 2014, which is a Section 371 U.S. National Stage application of PCT/US12/50615, entitled "System for Selecting a Stimulation Protocol Based on Sensed Respiratory Effort" filed Aug. 13, 2012, which claims the benefit of U.S. Provisional Patent Application No. 61/522,426, entitled "Method and System for Applying Stimulation in Treating Sleep Disordered Breathing," filed Aug. 11, 2011, all of which are incorporated herein by reference.

BACKGROUND

In cases in which sleep disordered breathing is caused by upper airway obstructions, one form of treatment includes stimulating one or more nerves that affect upper airway dilation. In a conventional technique, the stimulation is applied continuously or synchronized to the respiratory cycle. However, in some instances, continuous stimulation may not desirable because of any potential long-term effects of over-stimulating the nerve.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 is a diagram schematically illustrating respiratory cycles in one example breathing pattern, according to one example of the present disclosure.

FIG. 3 is a diagram schematically illustrating a first respiratory cycle exhibiting a flow limitation that occurs predominantly during an inspiratory phase and schematically illustrating a second respiratory cycle exhibiting mitigation of the flow limitation in response to a nerve stimulation protocol, according to one example of the present disclosure.

FIG. 4 is a diagram schematically illustrating a first respiratory cycle exhibiting a flow limitation that occurs predominantly during an expiratory phase and schematically illustrating a second respiratory cycle exhibiting mitigation of the flow limitation in response to a nerve stimulation protocol, according to one example of the present disclosure.

FIG. 5A is a diagram schematically illustrating a first respiratory cycle exhibiting a mixed flow limitation that overlaps a portion of an inspiratory phase and a portion of an expiratory phase and schematically illustrating a second respiratory cycle exhibiting mitigation of the flow limitation in response to one example nerve stimulation protocol, according to one example of the present disclosure.

FIGS. 8-13 are a series of diagrams with each diagram schematically illustrating a respiratory cycle during which one example nerve stimulation protocols is applied, according to one example of the present disclosure.

DETAILED DESCRIPTION

In the following Detailed Description, reference is made to the accompanying drawings which form a part hereof, and in which is shown specific examples of the present disclosure which may be practiced. In this regard, directional terminology, such as "top," "bottom," "front," "back," "leading," "trailing," etc., is used with reference to the orientation of the Figure(s) being described. Because components of examples of the present disclosure can be positioned in a number of different orientations, the directional terminology is used for purposes of illustration and is in no way limiting. It is to be understood that other examples may be utilized and structural or logical changes may be made without departing from the scope of the present disclosure. The following detailed description, therefore, is not to be taken in a limiting sense.

At least some examples of the present disclosure are directed to methods of treating obstructive sleep apnea via applying stimulation in intervals or periods during targeted portions of the respiratory cycle. By doing so, upper airway patency is maintained and/or increased while preventing collapse of the upper airway. At the same time, by using targeted stimulation, one can limit the overall volume of stimulation applied to a given nerve or set of nerves.

Figure 1A:
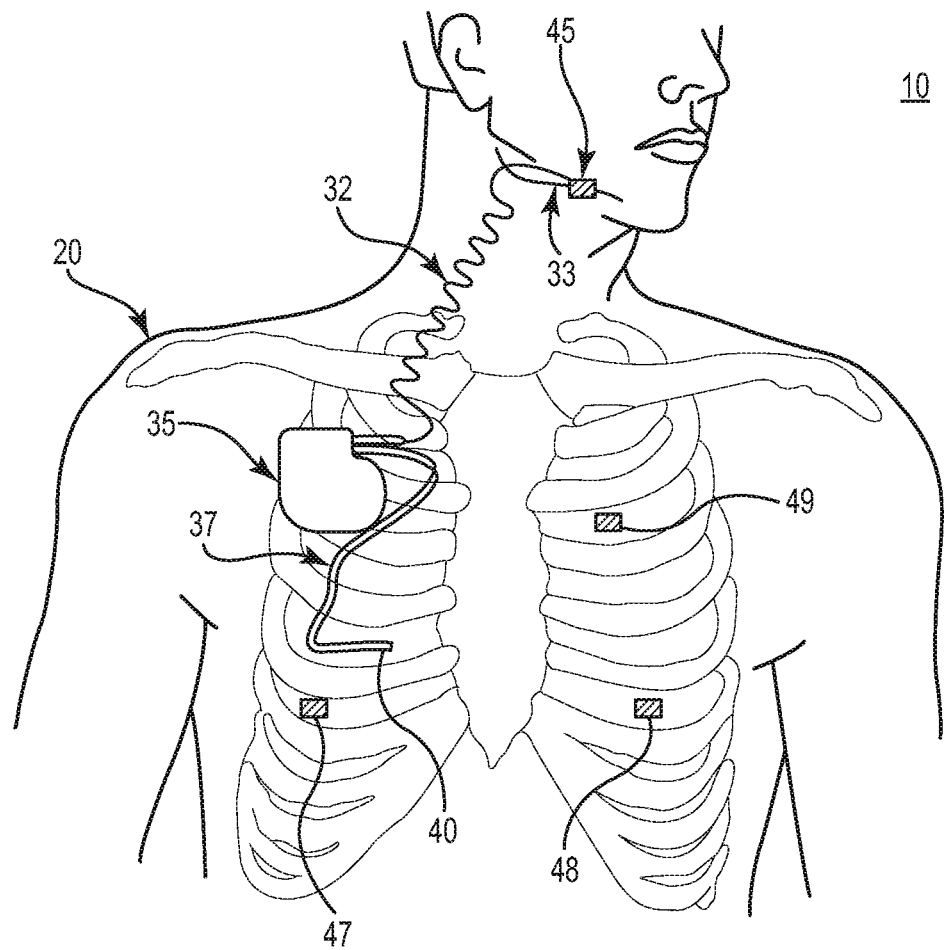
FIG. 1A is a schematic diagram of an at least partially implantable stimulation system relative to a patient, according to an example of the present disclosure.

FIG. 1A is a schematic diagram of an at least partially implantable stimulation system, according to an example of the present disclosure. As illustrated in FIG. 1A, in one example system 10 an implantable pulse generator (IPG) 35, capable of being surgically positioned within a pectoral region of a patient 20, and a stimulation lead 32 electrically coupled with the IPG 35 via a connector (not shown) positioned within a connection port of the IPG 35. The lead 32 includes a stimulation electrode portion 45 and extends from the IPG 35 so that the stimulation electrode portion 45 is positioned in contact with a desired nerve, such as the hypoglossal nerve 33 of the patient 10, to enable stimulation of the nerve 33, as described below in detail. An exemplary implantable stimulation system in which lead 32 may be utilized, for example, is described in U.S. Pat. No. 6,572,543 to Christopherson et al., and which is incorporated herein by reference in its entirety. In one embodiment, the lead 32 further includes at least one sensor portion 40 (electrically coupled to the IPG 35 and extending from the IPG 35) positioned in the patient 10 for sensing respiratory effort, such as respiratory pressure.

In some embodiments, the sensor portion 40 detects respiratory effort including respiratory patterns (e.g., inspiration, expiration, respiratory pause, etc.) in order to trigger activation of an electrode portion to stimulate a target nerve. Accordingly, with this arrangement, the IPG 35 (FIG. 1) receives sensor waveforms from the respiratory sensor portion 40, thereby enabling the IPG 35 to deliver electrical stimulation synchronously with inspiration (or synchronized relative to another aspect of the respiratory cycle) according to a therapeutic treatment regimen in accordance with examples of the present disclosure. It is also understood that the respiratory sensor portion 40 is powered by the IPG 35 and the IPG 35 also contains internal circuitry to accept and process the impedance signal from the stimulation lead 32.

In some embodiments, the sensor portion 40 is a pressure sensor. In one example, the pressure sensor in this embodiment detects pressure in the thorax of the patient. In other examples, the sensed pressure could be a combination of thoracic pressure and cardiac pressure (e.g., blood flow). With this configuration, the controller is configured to analyze this pressure sensing information to detect the respiratory patterns of the patient.

In some other embodiments, the respiratory sensor portion 40 comprises a bio-impedance sensor or pair of bio-impedance sensors and can be located in regions other than the pectoral region. In one aspect, such an impedance sensor is configured to sense a bio-impedance signal or pattern whereby the control unit evaluates respiratory patterns within the bio-impedance signal. For bio-impedance sensing, in one embodiment, electric current will be injected through an electrode portion within the body and an electrically conductive portion of a case of the IPG 35 (FIG. 3A) with the voltage being sensed between two spaced apart stimulation electrode portions (or also between one of the stimulation electrode portions and the electrically conductive portion of the case of IPG 35) to compute the impedance.

In some embodiments, system 10 also comprises additional sensors to further obtain physiologic data associated with respiratory functions. For example, system 10 may include various sensors (e.g., sensors 47, 48, 49 in FIG. 1) distributed about the chest area for measuring a transthoracic bio-impedance signal, an electrocardiogram (ECG) signal, or other respiratory-associated signals.

In some embodiments, the sensing and stimulation system for treating obstructive sleep apnea is a totally implantable system which provides therapeutic solutions for patients diagnosed with obstructive sleep apnea. In other embodiments, one or more components of the system are not implanted in a body of the patient. A few non-limiting examples of such non-implanted components include external sensors (respiration, impedance, etc.), an external processing unit, or an external power source. Of course, it is further understood that the implanted portion(s) of the system provides a communication pathway to enable transmission of data and/or controls signals both to and from the implanted portions of the system relative to the external portions of the system. The communication pathway includes a radiofrequency (RF) telemetry link or other wireless communication protocols.

Whether partially implantable or totally implantable, the system is designed to stimulate the hypoglossal nerve during some portion of the repeating respiratory cycle to thereby prevent obstructions or occlusions in the upper airway during sleep. In one embodiment, the implantable system comprises an implantable pulse generator (IPG), a peripheral nerve cuff stimulation lead, and a pressure sensing lead.

Figure 1B:
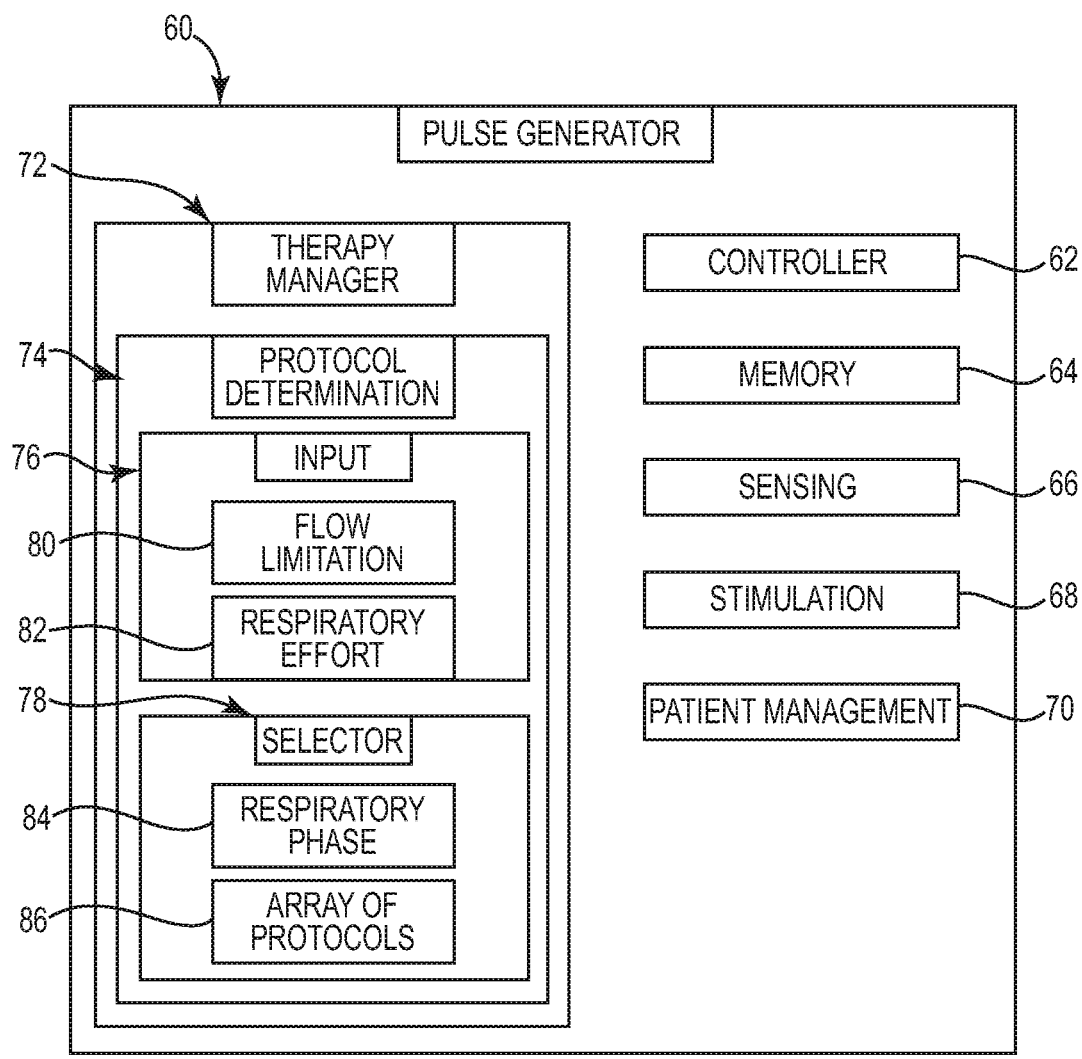
FIG. 1B is a block diagram schematically illustrating a pulse generator, according to one example of the present disclosure.

FIG. 1B is a block diagram schematically illustrating an implantable pulse generator (IPG) 60, according to one example of the present disclosure. In one embodiment, IPG 60 generally includes at least substantially the same features and attributes as IPG 35 of FIG. 1A. As illustrated in FIG. 1B, in one example, implantable pulse generator 60 includes controller 62, memory 64, sensing module 66, stimulation module 68, patient management module 70, and a therapy manager 72.

Via an array of parameters, the sensing module 66 receives and tracks signals from various physiologic sensors (such as a pressure sensor, blood oxygenation sensor, acoustic sensor, electrocardiogram (ECG) sensor, or impedance sensor) in order to determine a respiratory state of a patient, whether or not the patient is asleep or awake, and other respiratory-associated indicators, etc. Such respiratory detection may be received from either a single sensor or any multiple of sensors, or combination of various physiologic sensors which may provide a more reliable and accurate signal. In one example, sensing module 90 receives signals from sensor portion 40 and/or sensors 47, 48, 49 in FIG. 1A.

In one example, a controller 62 of IPG 60 comprises one or more processing units and associated memories configured to generate control signals directing the operation of IPG 60 and system 10 (FIG. 1A). In particular, in response to or based upon commands received via an input and/or machine readable instructions (including software) contained in the memory 64 associated with the controller 62 in response to physiologic data gathered via the sensors, controller 62 generates control signals directing operation of pulse generator 60 to selectively control stimulation of a target nerve, such as the hypoglossal nerve, to restore airway patency and thereby reduce or eliminate apnea events. In one example, controller 62 is embodied in a general purpose computer.

For purposes of this application, in reference to the controller 62, the term "processor" shall mean a presently developed or future developed processor (or processing resources) that executes sequences of machine readable instructions (such as but not limited to software) contained in a memory. Execution of the sequences of machine readable instructions causes the processor to perform actions, such as operating IPG 60 to provide apply stimulation to a nerve in the manner described in the examples of the present disclosure. The machine readable instructions may be loaded in a random access memory (RAM) for execution by the processor from their stored location in a read only memory (ROM), a mass storage device, or some other persistent storage or non-volatile form of memory, as represented by memory 64. In one example, memory 64 comprises a computer readable medium providing non-transitory or non-volatile storage of the machine readable instructions executable by a process of controller 62. In other examples, hard wired circuitry may be used in place of or in combination with machine readable instructions (including software) to implement the functions described. For example, controller 62 may be embodied as part of at least one application-specific integrated circuit (ASIC). In at least some examples, the controller 62 is not limited to any specific combination of hardware circuitry and machine readable instructions (including software), nor limited to any particular source for the machine readable instructions executed by the controller 62.

With this in mind, in general terms the therapy manager 72 acts to synthesize respiratory information, to determine suitable stimulation parameters based on that respiratory information, and to direct electrical stimulation to the target nerve.

In one example, among other components, therapy manager 72 includes a stimulation protocol determination module 74.

In one example, the stimulation protocol determination module 74 includes an input function 76 and a selector function 78. In general terms, the input function receives an indication of an upper airway flow limitation that is sensed via respiratory effort information. In one example, input function 76 includes a flow limitation parameter 80 and a respiratory effort parameter 82.

In one example, the flow limitation parameter 80 detects and tracks when a flow limitation is present in the upper airway of a patient. In one aspect, the flow limitation parameter 80 tracks the degree and/or duration of flow limitation. Various examples of recognizing a flow limitation are further described below in association with at least FIGS. 3-13.

In one example, the respiratory effort parameter 82 detects and tracks respiratory effort information obtained via sensing respiratory information such as, but not limited to, the respiratory sensing methods previously described above in association with FIGS. 1A-1B. This respiratory effort information corresponds to air flow and enables constructing or determining a degree and/or duration of a flow limitation in the upper airway of a patient.

As noted above, the therapy manager 72 also includes a selector function 78, which in general terms, enables the IPG 60 to select an appropriate stimulation protocol that is responsive to a particular type of upper airway flow limitation. In one example, the selector function 78 includes a respiratory phase parameter 84 and a protocol array parameter 86. The respiratory phase parameter 84 determines which respiratory phase or phases, or portions of the respective phases, in which stimulation should be applied. In one aspect, these determinations are made based on the ongoing sensing of respiratory effort, with the sensed information being received by input function 76.

The protocol array parameter 86 provides an array of stimulation protocols suitable for delivering to a nerve of a patient, depending upon the type, degree, and/or duration of a flow limitation. The protocol array parameter 86 does so in cooperation with respiratory phase parameter 84 and input function 76.

Specific examples of treating disordered breathing via the therapy manager 72, and in particular, treating upper airway flow limitations (i.e. obstructions) via the functions, components, parameters, and/or features of protocol determination module 74 of therapy manager 72 are further described and illustrated below in association with FIGS. 3-13.

In general terms, the stimulation module 68 of IPG 60 is configured to generate and apply a neuro-stimulation signal via electrode(s) (such as stimulation electrode(s) 45 in FIG. 1A) according to a treatment regimen programmed by a physician and/or in cooperation with therapy manager 72, such as via protocol determination module 74.

In general terms, the patient management module 70 is configured to facilitate communication to and from the IPG 60 in a manner familiar to those skilled in the art. Accordingly, the patient management module 70 is configured to report activities of the IPG 70 (including sensed physiologic data, stimulation history, number of apneas detected, etc.) and is configured to receive initial or further programming of the IPG 60 from an external source, such as a patient programmer, clinician programmer, etc.

Figure 1C:
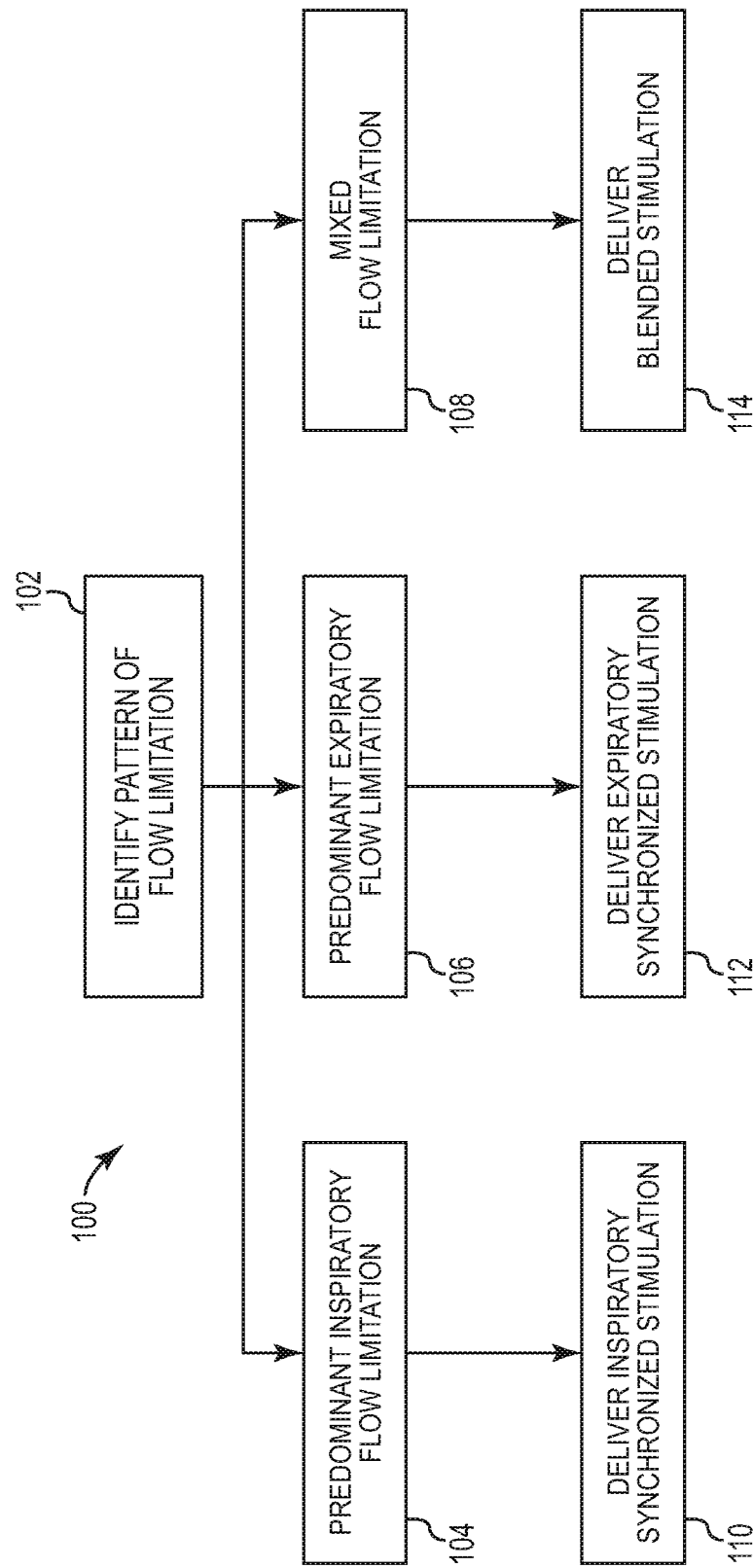
FIG. 1C is flow diagram schematically illustrating a method of treating an upper airway flow limitation, according to one example of the present disclosure.

In one example, as shown in FIG. 1C, prior to applying stimulation to maintain and/or restore patency in the upper airway, at 102 the method 100 includes identifying a pattern of flow limitation during the respiratory cycle. In one aspect, method 100 identifies the circumstances in which a flow limitation primarily occurs. In particular, with further reference to FIG. 1, method 100 distinguishes between a flow limitation occurring: (1) predominantly during inspiration (at 104); (2) predominantly during expiration (at 106); or (3) during both a portion of inspiration and a portion of expiration which acts as a mixed flow limitation (at 108). In one aspect, in the context of the present disclosure, a flow limitation corresponds to a narrowing of the upper airway of the type typically associated with obstructive sleep apnea or other disordered breathing patterns, as familiar to those skilled in the art.

As shown in FIG. 1C, in one example, in the event that the flow limitation occurs predominantly during inspiration (at 104), then stimulation is applied during and/or synchronized with inspiration (at 110). On the other hand, in another example, in the event that the flow limitation occurs predominantly during (i.e. coincides with) expiration (at 106), and then stimulation is applied during and/or synchronized with expiration (at 112).

However, in some examples, when the flow limitation occurs predominantly during (i.e. coincides with) a portion of inspiration and a portion of expiration (at 108), the stimulation is applied during some portion of inspiration and some portion of expiration (at 114).

In one example, when the flow limitation overlaps the transition between the end of inspiration and the beginning of expiration, the stimulation will be applied to overlap the transition between the end of inspiration and the beginning of expiration.

In another example, when the flow limitation occurs during a portion of inspiration and a portion of expiration (at 108), the stimulation is applied to cover an entire respiratory cycle, including an entire inspiratory phase and an entire expiratory phase.

In order to recognize a flow limitation, the method 100 uses as a reference point a normal breathing pattern 150, as shown in FIG. 2. Of course, variances may exist from patient-to-patient so it will be understood that the normal breathing pattern 150 is a representative example provided for illustrative purposes and is not intended to strictly define a breathing pattern that is universally normal for all patients. With this in mind, in some embodiments, the method 100 uses the particular breathing pattern of a specific patient (to which the method is applied) as the reference point to evaluate the presence or absence of a flow limitation in breathing.

In the example of normal breathing pattern 150 shown in FIG. 2, a respiratory cycle 160 includes an inspiratory phase 162 and an expiratory phase 170. The inspiratory phase 162 includes an initial portion 164, intermediate portion 165, and end portion 166 while expiratory phase 170 includes an initial portion 174, intermediate portion 175, end portion 176, and an expiratory peak 177. A first transition 180 occurs at a junction between the end inspiratory portion 166 and the initial expiratory portion 174 while a second transition 182 occurs at a junction between the end expiratory portion 176 and the initial inspiratory portion 164.

In one example, the various stimulation protocols described and illustrated in association with FIGS. 3-13 are implemented via system 10 (FIG. 1A) and/or IPG 60 (FIG. 1B) including at least therapy manager 72 and/or protocol determination module 74. However, in another example, the various stimulation protocols described and illustrated in association with FIGS. 3-13 are implemented via other component, modules, and systems.

FIG. 3 is a diagram 200 illustrating a disordered breathing pattern 203A and treated breathing pattern 203B (separated by dashed line 203C), according to one embodiment of the present disclosure. As shown in FIG. 3, disordered breathing pattern 203A reflects the presence of a flow limitation in the upper airway that occurs predominantly during the inspiratory phase of a respiratory cycle. The inspiratory phase 202A includes an initial portion 204A, an intermediate portion 205A, and an end portion 206A while the expiratory phase 210A includes an initial portion 214A, intermediate portion 215A, peak 217A, and end portion 216A. In one aspect, intermediate portion 205A of inspiratory phase 202A forms a generally flat or horizontal shape corresponding to a substantially truncated amplitude (as compared to a normal breathing pattern, such as FIG. 2) and that reflects the occurrence of a flow limitation (symbolically represented by arrow 201) in the upper airway during inspiration. However, via application of stimulation (symbolically represented by bar 221), breathing is restored as represented by treated breathing pattern 202B in which intermediate portion 205B of inspiratory phase 202B resumes a generally parabolic shape corresponding to a generally normal amplitude and that represents amelioration of the flow limitation. In one embodiment, the stimulation is represented by bar 221, which extends from a first end 222 to a second end 224, with the stimulation substantially coinciding with the entire duration of the inspiratory phase 202B. As shown in FIG. 3, the stimulation 221 terminates prior to the expiratory phase 210B. However, as will be explained in more detail below, in other embodiments, the applied stimulation does not extend the entire duration of inspiratory phase 202B but is applied to select portions of the inspiratory phase 202B.

It will be understood that, in one example, the detection of flow limitations and/or associated apneas), as well as the detection of the beginning and end of the respective inspiratory and expiratory phases of the respiratory cycle to enable determining when to stop or start stimulation, is performed according to, or in cooperation with, known methods and devices for doing so. Some non-limiting examples of such devices and methods to recognize and detect the various features and patterns associated with respiratory effort and flow limitations include, but are not limited to: PCT Publication WO/2010/059839, titled A METHOD OF TREATING SLEEP APNEA, published on May 27, 2010; Christopherson U.S. Pat. No. 5,944,680, titled RESPIRATORY EFFORT DETECTION METHOD AND APPARATUS; and Testerman U.S. Pat. No. 5,522,862, titled METHOD AND APPARATUS FOR TREATING OBSTRUCTIVE SLEEP APNEA.

FIG. 4 is a diagram 250 illustrating a disordered breathing pattern 253A and treated breathing pattern 253B, according to one embodiment of the present disclosure. As shown in FIG. 4, disordered breathing pattern 253A reflects the presence of a flow limitation in the upper airway that occurs predominantly during the expiratory phase of a respiratory cycle. In the disordered breathing pattern 253A, the inspiratory phase 252A includes an initial portion 254A, an intermediate portion 255A, and an end portion 256A, with the inspiratory phase 252A exhibiting a generally normal breathing pattern 150 (FIG. 2). Referring again to FIG. 4, the expiratory phase 262A includes an initial portion 264A, intermediate portion 265A, peak 267A, and end portion 266A. In one aspect, expiratory phase 262A has a relatively shallow peak 267A corresponding to an amplitude or peak pressure that is substantially smaller than a peak 177 of an expiratory phase 170 in a normal breathing pattern 150 (FIG. 2). The pattern of expiratory phase 262A, which corresponds to a generally shallow expiration, reflects the occurrence of a flow limitation (symbolically represented by arrow 251) in the upper airway during expiration. Moreover, because the peak 267A is so shallow, the intermediate portion 265A in the expiratory phase 262A has a relatively gradual upward slope instead of the generally steep upward slope present in the intermediate portion 175 in the normal expiratory phase 170 (of a normal breathing pattern 150 in FIG. 2).

However, as shown in FIG. 4, via application of stimulation (symbolically represented by bar 270), the expiratory phase 262B becomes corrected such that peak 267B resumes its full amplitude and intermediate portion 265B of expiratory phase 262B is restored to a generally steep upward slope, both of which represents amelioration of the flow limitation. In one embodiment, the stimulation (270) is represented by bar 271 (which extends from a first end 272 to a second end 274) and substantially coincides with the entire duration of the expiratory phase 262B. However, as will be explained in more detail below, in other embodiments, the applied stimulation extends only part of the duration of expiratory phase 262B.

In one embodiment, application of the stimulus occurs at an inspiratory phase (FIG. 3) or at an expiratory phase (FIG. 4), respectively, of every respiratory cycle. However, in other embodiments, application of the stimulus is applied selectively to just some respiratory cycles, as needed, in association with an auto-titration method. One example of such auto-titration methods include A METHOD OF TREATING SLEEP APNEA as described and illustrated in PCT Publication WO/2010/059839, published on May 27, 2010.

FIG. 5A is a diagram 280 illustrating a disordered breathing pattern 283A and treated breathing pattern 283B, according to one embodiment of the present disclosure. As shown in FIG. 5A, disordered breathing pattern 283A represents a flow limitation in the upper airway that occurs during both a portion of an inspiratory phase 282 and a portion of the expiratory phase 292 of a respiratory cycle. As shown in FIG. 5A, the inspiratory phase 282A includes an initial portion 284A, an intermediate portion 285A, and an end portion 286A while the expiratory phase 292A includes an initial portion 294A, intermediate portion 295A, peak 297A, and end portion 296A.

In one aspect, FIG. 5A illustrates that in disordered breathing pattern 283A, intermediate portion 285A of inspiratory phase 282A forms a generally flat or horizontal shape corresponding to a substantially truncated amplitude (as compared to the inspiratory phase 162 of a normal breathing pattern 150, such as FIG. 2), with this generally flat shape reflecting the occurrence of a flow limitation (symbolically represented by arrow 281A) in the upper airway during inspiration.

In another aspect, disordered breathing pattern 283A also includes an expiratory phase 292A having a peak 297A corresponding to an amplitude or peak pressure that is substantially smaller than a peak 177 of an expiratory phase 170 in a normal breathing pattern 150 (FIG. 2). This pattern 283A, which corresponds to generally shallow expiration, results from a flow limitation (symbolically represented by arrow 281B) in the upper airway during expiration. Moreover, because the peak 297A is so shallow, the intermediate portion 295A has a relatively gradual upward slope instead of the generally steep upward slope present in the intermediate portion 175 in the normal expiratory phase 170 (of a normal breathing pattern 150 in FIG. 2).

In one example, the indicated upper airway flow limitation predominantly coincides with both of a first portion of the inspiratory phase and a first portion of the expiratory phase. In another aspect, this indicated flow limitation does not predominantly coincide with a second portion of inspiratory phase and with a second portion of the expiratory phase.

However, via application of blended stimulation (symbolically represented by bar 300) directed to at least a portion of the inspiratory phase and a portion of the expiratory phase, the flow limitations are mitigated. As shown in treated breathing pattern 283B, a latter segment 285C of intermediate portion 285B (and end portion 286B) resumes a more parabolic shape better resembling a baseline inspiratory phase prior to the flow limitation and that corresponds to amelioration of the "inspiratory" flow limitation.

Likewise, because this stimulation overlaps from the inspiratory phase 282B into the expiratory phase 292B, the treated breathing pattern 283B exhibits a peak 297B approaching a baseline amplitude prior to the flow limitation (like amplitude 177 in the expiratory phase 170 of normal breathing pattern 150 of FIG. 2). This treated breathing pattern 283B also exhibits an intermediate portion 295B that is restored to steeper upward slope amplitude, both of which represents amelioration of the "expiratory" flow limitation.

In one embodiment, the stimulation is represented by bar 300, which extends from a first end 301 (in the inspiratory phase 282B) to a second end 303 (in the expiratory phase 292B). The stimulation is applied as a generally continuous stimulation period that is initiated (at a start point located away from a beginning portion 284B of the inspiratory phase 252B) from partway through the intermediate portion 285B and through the end portion 285C of the inspiratory phase 282B, through the transition from inspiration to expiration, through the initial portion 294B and peak 297A of the expiratory phase 292B, and at least partway through the intermediate portion 295B of the expiratory phase 292B (to a termination point prior to end portion 296B of expiratory phase 292B).

In one example, the embodiment of FIG. 5A addresses the situation for some patients in which the greatest risk for airway collapse appears to occur near the end of inspiration and the beginning of expiration. In these instances, besides harmfully limiting a duration and volume of inspiration, a partially restricted upper airway throughout the inspiratory phase predisposes the upper airway to be more susceptible to further collapse at the end of the inspiratory phase and/or to the beginning of the expiratory phase. Accordingly, in the embodiment of FIG. 5A, the blended stimulation (represented by bar 300) begins at start point approximately midway through the inspiratory phase 282B and extends substantially continuously through a transition between the end of inspiration and the beginning of expiration until reaching a termination point approximately midway through the expiratory phase 292B. In one aspect, this blended stimulation is terminated after a bulk of the expiration would have been expected to occur. In this way, continuous stimulation of the hypoglossal nerve through complete respiratory cycles is avoided, which in turn, minimizes unnecessary stimulation of the hypoglossal nerve. Instead, in these embodiments, stimulation is applied strategically in targeted portions of one or more respiratory cycles to prevent upper airway collapse so that stimulation is applied more judiciously while still achieving efficacious results.

Further, it will be understood that diagram 280 in FIG. 5A provides just one example schematically illustrating the application of a blended stimulation that overlaps the end of the inspiratory phase and the beginning of the expiratory phase.

Accordingly, applying this blended stimulation overcomes expiratory narrowing, which otherwise might render the upper airway vulnerable to complete collapse during a subsequent inspiratory effort.

Without being bound to any particular theory, it is believed that the blended stimulation that overlaps the end of inspiratory phase and the expiratory phase acts to maintain a minimum level of pressurization within the lungs, which in turn helps maintain airway patency because the minimum level of pressurization helps to prevent a high intensity vacuum from the lungs on the airway, which would otherwise potentially cause collapse of the upper airway.

In this way, for some patients, the stimulation is applied during a period having a higher risk for collapse without having to continuously apply stimulation through the entire respiratory cycle, which in turn, saves energy and minimizes potentially unnecessary stimulation of the nerves.

In one example of a stimulation protocol, such as the one described and illustrated in association with FIG. 5A, the generally continuous stimulation period (as represented by bar 300 in FIG. 5A and spanning over a portion of the inspiratory phase and a portion of the expiratory phase) is applied to a set of consecutive respiratory cycles over a first time period. Moreover, an input module (such as input module 76 of protocol determination module 74 of therapy manager 72 in FIG. 1B) is configured to evaluate whether flow limitations are persisting despite the stimulation protocol or whether the stimulation protocol has mitigated or eliminated the previously occurring flow limitations. Accordingly, in one aspect, the input module of the therapy manager determines if at least some indications of upper airway flow limitations are received within the first time period. In another aspect, the input module of the therapy manager increases a duration of the generally continuous stimulation period if the input module receives the at least some indications during the first time period when such indications exceed a threshold. In another aspect, the input module of the therapy manager reduces the duration of the generally continuous stimulation period if the input module receives no indications of upper airway flow limitations (or a number of indications less than a threshold) during the first time period.

In one example, the first time period (over which the set of respiratory cycles take place) is a duration, based on an apnea-hypopnea index of a patient, in which an apnea would be expected to occur in the absence of stimulation.

Figure 5B:
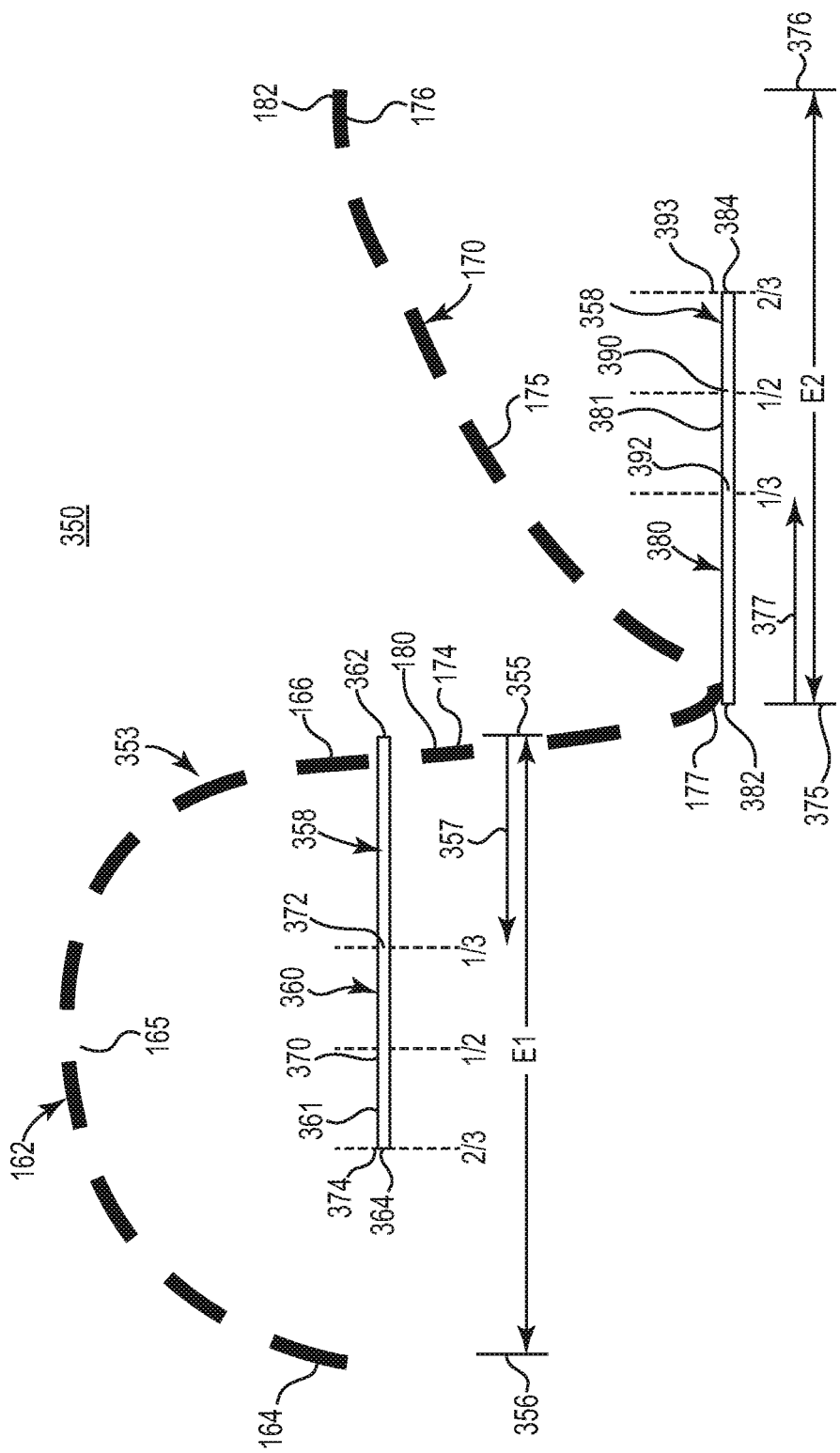
FIG. 5B is a diagram schematically illustrating portions of a generally continuous stimulation period relative to portions of the respective inspiratory and expiratory phases of a respiratory cycle, according to one example of the present disclosure.

FIG. 5B is a diagram schematically illustrating portions of a generally continuous stimulation period relative to portions of an inspiratory phase and an expiratory phase, according to one example of the present disclosure.

As a reference point for illustrating the generally continuous stimulation period, FIG. 5B provides substantially the same depiction of a respiratory cycle 160 that was previously shown in FIG. 1. Accordingly, the illustrated respiratory cycle 160 includes an inspiratory phase 162 and an expiratory phase 170. The inspiratory phase 162 includes an initial portion 164, intermediate portion 165, and end portion 166 while expiratory phase 170 includes an initial portion 174, intermediate portion 175, end portion 176, and an expiratory peak 177. A first transition 180 occurs at a junction between the end inspiratory portion 166 and the initial expiratory portion 174 while a second transition 182 occurs at a junction between the end expiratory portion 176 and the initial inspiratory portion 164.

According to one example of the present disclosure, FIG. 5B further illustrates a first bar 361 that represents a first portion 360 of a generally continuous stimulation period 358 and a bar 381 that represents a second portion 380 of a generally continuous stimulation period 358. As shown in FIG. 5B, the bar 361 includes first end 362 that generally coincides with junction 180 (the end of inspiratory phase 162 and beginning of expiratory phase 170) and a second end 364 located in an intermediate portion of the inspiratory phase 162. As shown in FIG. 5B, bar 381 includes first end 382 that generally coincides with junction 180 (the end of inspiratory phase 162 and beginning of expiratory phase 170) and a second end 384 located in an intermediate portion of the expiratory phase 170.

As further demonstrated by FIG. 5B, while the generally continuous stimulation period overlaps the inspiratory and expiratory phases 162, 170, the duration of each of the first and second portions of the generally continuous stimulation period can vary among different nerve stimulation protocols as determined by the protocol determination module 74 of therapy manager 72 (FIG. 1B).

In one example, the first portion 360 of the generally continuous stimulation period 358 has a duration of at least one-third (identified by marker 372) of an entirety (E1) of the inspiratory phase 162. In one aspect, the relative proportion of one-third is measured starting at end 362 of bar 361, per directional reference arrow 357. In another example, the first portion 360 of the generally continuous stimulation period 358 has a duration of at least one-half (identified by marker 370) of the entirety (E1) of the inspiratory phase 162. In another example, the first portion 360 of the generally continuous stimulation period 358 has a duration of at least two-thirds (identified by marker 374) of the entirety (E1) of the inspiratory phase 162

In another example, the second portion 380 of the generally continuous stimulation period 358 has a duration of at least one-third (identified by marker 392) of an entirety (E2) of the expiratory phase 170. In one aspect, the relative proportion of one-third is measured starting at end 382 of bar 381, per directional reference arrow 377. In another example, the first portion 380 of the generally continuous stimulation period 358 has a duration of at least one-half (identified by marker 390) of the entirety (E2) of the expiratory phase 170. In another example, the first portion 380 of the generally continuous stimulation period 358 has a duration of at least two-thirds (identified by marker 393) of the entirety (E2) of the expiratory phase 170.

In one example, the first portion (during which stimulation is applied) of the inspiratory phase 162 corresponds to at least a majority of an entirety (E1) of the inspiratory phase 162 and the first portion (during which stimulation is applied) of the expiratory phase 170 corresponds to at least a majority of an entirety (E2) of the expiratory phase 170. In one example, a majority is defined as at least fifty-one percent (i.e. 51%). In another example, the majority of the inspiratory phase 162 is defined as at least two-thirds majority of the entirety (E1) of the inspiratory phase 162 and the majority of the expiratory phase is defined as an at least two-thirds majority of the entirety (E2) of the expiratory phase 170.

In one example, variations on the stimulation protocol associated with FIGS. 5A and 5B are further described later in association with at least FIGS. 6 and 11.

Figure 6:
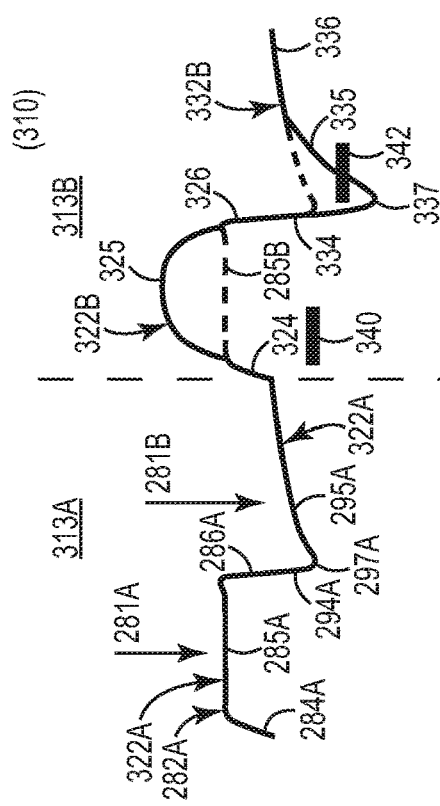
FIG. 6 is a diagram schematically illustrating a first respiratory cycle exhibiting a mixed flow limitation that overlaps a portion of an inspiratory phase and a portion of an expiratory phase and schematically illustrating a second respiratory cycle exhibiting mitigation of the flow limitation in response to one example nerve stimulation protocol, according to one example of the present disclosure.

In another embodiment, as shown in FIG. 6, diagram 310 schematically illustrates a disordered breathing pattern 333A resulting from a mixed flow limitation that is substantially similar to the mixed flow limitation in FIG. 5A. However, unlike the substantially continuous segment of stimulation 300 applied in FIG. 5A, in the embodiment shown in FIG. 6, stimulation is applied in two separate relatively short bursts 340, 342. One burst 340 is applied at the beginning of the inspiratory phase 322B while the other burst 342 is applied at the beginning of the expiratory phase 332B. In this embodiment, the stimulation is targeted to anticipate an obstruction, and in turn, apply stimulation at the beginning of one or both of the respective inspiratory and expiratory phases. By stimulating (for a short duration) at the beginning of a respective inspiratory and expiratory phases, the upper airway is held open prior to the maximum flow of air in that phase so that once the flow of air commences, with the upper airway already open to a generally full degree, the inspired or expelled air (respectively) completes the job of maintaining the upper airway in the open state during the remainder of the respective inspiratory or expiratory phase. In another aspect, one potential benefit from applying a stimulation burst at the beginning of an inspiratory phase is the resulting counteraction of the negative pressure (generated by the inspiratory effort) applied to the upper airway.

Without being bound to any particular theory, it is believed that by applying a stimulation burst (e.g., an additional stimulation burst on top of a baseline level of stimulation or an isolated burst of stimulation without a baseline level of stimulation) at the beginning of the inspiratory phase, the stimulation causes or ensures radial expansion of the airway at the very time that a high intensity vacuum would be applied (via the lungs) to the upper airway such that the radial expansion of the upper airway (caused by the stimulation burst) directs action or response of tissues in a direction opposite the action of tissue that would might otherwise occur when the vacuum from lungs acts on the upper airway tissues. Accordingly, the stimulation is timed to produce momentum in the tissues of the upper airway toward radial expansion prior to the high intensity vacuum pull (which might otherwise contribute to collapse of the upper airway) from the lungs during the onset of inspiration. Because there is a delay associated with, or caused by, a time constant in the response of the upper airway tissues, by first stimulating the tissue in advance of the vacuum pull from the lungs, enough momentum is established toward radial expansion of the upper airway via the stimulation burst that this momentum counteracts or prophylactically negates the otherwise potentially collapsing effects of the vacuum pull on the upper airway tissues.

In one aspect, by applying stimulation in this manner, it is believed that airway patency is maintained with less overall stimulation being applied because stimulation is applied strategically within one or more respiratory cycles rather than indiscriminately through entire respiratory cycles. With this in mind, in one embodiment the total combined duration of burst 340 and burst 342 (shown in FIG. 6) is substantially less than the duration of the stimulation pulse 300 in FIG. 5A. Accordingly, adequate airway patency is achieved while significantly reducing the total volume of stimulation applied to the nerve.

In some embodiments in which separate bursts of stimulation are applied to the inspiratory and expiratory phases, respectively, the duration of the bursts in the inspiratory phase differ from the duration of the burst applied in the expiratory phase. For example, as shown in the diagram 400 of FIG. 7A, a representative or normal breathing pattern 401 is maintained by applied stimulation. A stimulation burst (represented by bar 420A) of a first duration is applied at the beginning of the inspiratory phase 402A while a second stimulation burst (represented by bar 422A) is applied during substantially the entire expiratory phase 412A. This pattern of stimulation bursts is repeated throughout successive respiratory cycles 402B, 402C, etc.

In one aspect, the determination regarding the duration of each "inspiratory phase" burst (420A, 420B, 420C) and the duration of each "expiratory phase" burst (422A, 422B, 422C) can vary from patient-to-patient depending upon whether the particular patient tends to exhibit a greater flow limitation in the inspiratory phase 403A or in the expiratory phase 413A. In the example, shown in FIG. 7A, the "expiratory phase" bursts (422A, 422B, 422C) have a longer duration than the "inspiratory phase" bursts (420A, 420B, 420C) to treat a patient that generally exhibits a mixed flow limitation (both inspiratory and expiratory) but having greater flow limitations during the expiratory phase.

In one embodiment, anyone of or all of an amplitude, a pulse width, a frequency of applied stimulation during the inspiratory phase is different than anyone of (or all of) an amplitude, a pulse width, a frequency of applied stimulation during the expiratory phase. In addition, a ramped stimulation pattern in which stimulation ramps upward (increases) at the beginning of a stimulation period or ramps downward at the end of a stimulation period, can be applied in one or both of the inspiratory and expiratory phases.

Figure 7A:
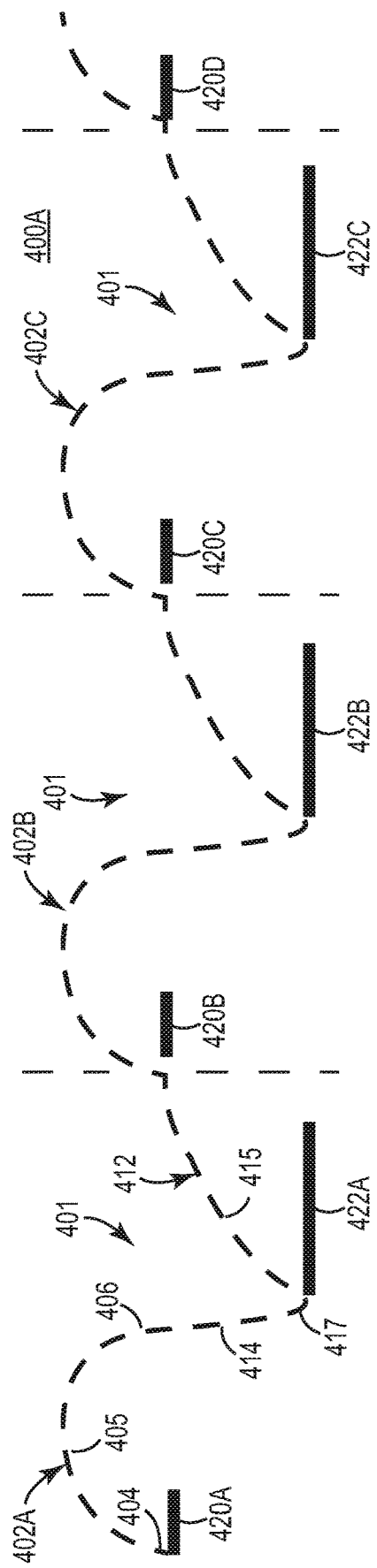
FIGS. 7A-7B are a pair of diagrams with each diagram schematically illustrating a series of respiratory cycles during which one example nerve stimulation protocol is applied, according to one example of the present disclosure.
Figure 7B:
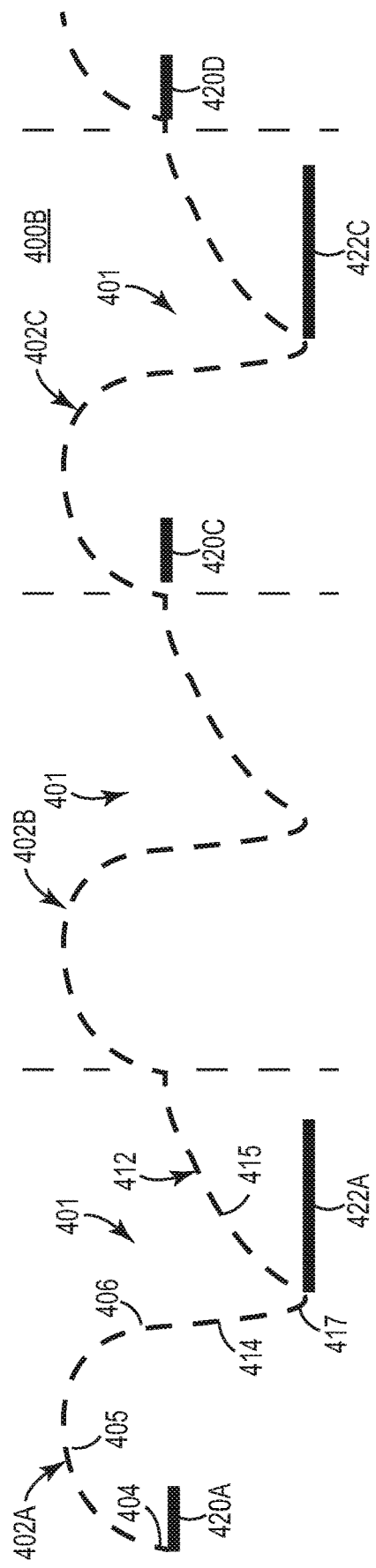

In some embodiments, as shown in FIG. 7B, instead of applying a stimulation burst with each respiratory cycle, the stimulation bursts (e.g. 420A, 420C, 422A, 422C) are applied every other respiratory cycle, such that an intermediate "inspiratory phase" burst 422A and an intermediate "expiratory phase" burst 422B are omitted. In this embodiment, the patient need not receive a stimulation burst each respiratory cycle because with this stimulation pattern the patient receives enough oxygen to keep the respiratory drive in equilibrium. In another embodiment, the pattern of stimulation bursts in the inspiratory phase (applied every respiratory cycle, such as 420A, 420B, 420C) need not be matched by the pattern of stimulation bursts in the expiratory phase (applied every other respiratory cycle, such as 422A and 422C), or vice versa. In this way, the upper airway remains patent and the patient receives sufficient oxygen without receiving stimulation in each inspiratory phase or in each expiratory phase.

In yet other embodiments, other forms of alternating stimulation bursts are applied. For example, in one pattern of stimulation, a low amplitude continuous pulsed stimulation is applied and one or more relatively shorter duration stimulation bursts are applied in a targeted and additive manner to the low amplitude continuous stimulation. FIG. 8 is a diagram 450 schematically illustrating a method of treating sleep disordered breathing via a stimulation pattern, according to one embodiment of the present disclosure. As shown in FIG. 8, a respiratory cycle 453 includes an inspiratory phase 451 and an expiratory phase 461. The inspiratory phase 451 includes an initial portion 454, an intermediate portion 455, and an end portion 456 while the expiratory phase 461 includes an initial portion 464, intermediate portion 465, peak 467, and end portion 466.

As further shown in the diagram 450 of FIG. 8, a low amplitude continuous pulsed stimulation (represented by bar 470) is applied in the inspiratory phase 451 and a low amplitude pulsed continuous stimulation (represented by bar 480) in the expiratory phase 461. While bars 470, 480 are shown as separate elements for illustrative purposes, it will be understood that the generally continuous stimulation is substantially uninterrupted through the transition from the inspiratory phase 451 to the expiratory phase 461. In addition, as shown in FIG. 8, a shorter duration stimulation burst 475 is applied only in the inspiratory phase 451 (for patients having predominantly inspiratory-based flow limitations) in addition to the generally continuous pulsed lower amplitude tone stimulation 470. While the additional stimulation burst 475 could be applied anywhere within the inspiratory phase 451, in the example shown in FIG. 8, the burst is applied at the initial portion 454 of the inspiratory phase 451. In one aspect, applying the burst at the initial portion 454 helps to ensure full patency of the upper airway as inspiration begins because the stimulation causes a response like the action of a virtual stent in the upper airway to pre-establish patency prior to the vacuum pull from the lungs. As previously noted, the initial portion of stimulation (during a peak pressure period) effectively establishes momentum of the upper airway to be moving in direction of expansion (radially outward) such that upon a vacuum applied via the lungs during inspiration, the upper airway tends to stay expanded because response of tissue is slow enough such that the vacuum (generated by the lungs) cannot fully overcome the already established momentum of radial expansion of the upper airway and therefore the initial portion of stimulation prevents collapse of the upper airway.

Without being bound by any particular theory, it is believed that using a burst of stimulation (for example, burst 475 in FIG. 8) helps to keep blood oxygenation levels and carbon dioxide levels within an acceptable range, which in turn moderates the respiratory drive, which in turn minimizes peak respiratory pressures. Together, these factors minimizes the risk of an upper airway collapse because the lungs are not forced (via the respiratory drive) to exert extra vacuum pressure on an upper airway in an attempt to acquire more oxygen.

In one embodiment, the stimulation pattern in FIG. 8 is modified, such that the modified pattern omits the base level of generally continuous stimulation 470 in the inspiratory phase 451, leaving just one or more stimulation bursts 475 in the inspiratory phase 451. Meanwhile, the modified pattern retains the base level stimulation 480 during the expiratory phase 461, which effectively acts to maintain tone and patency of the upper airway during the expiratory phase 461.

Figure 9:
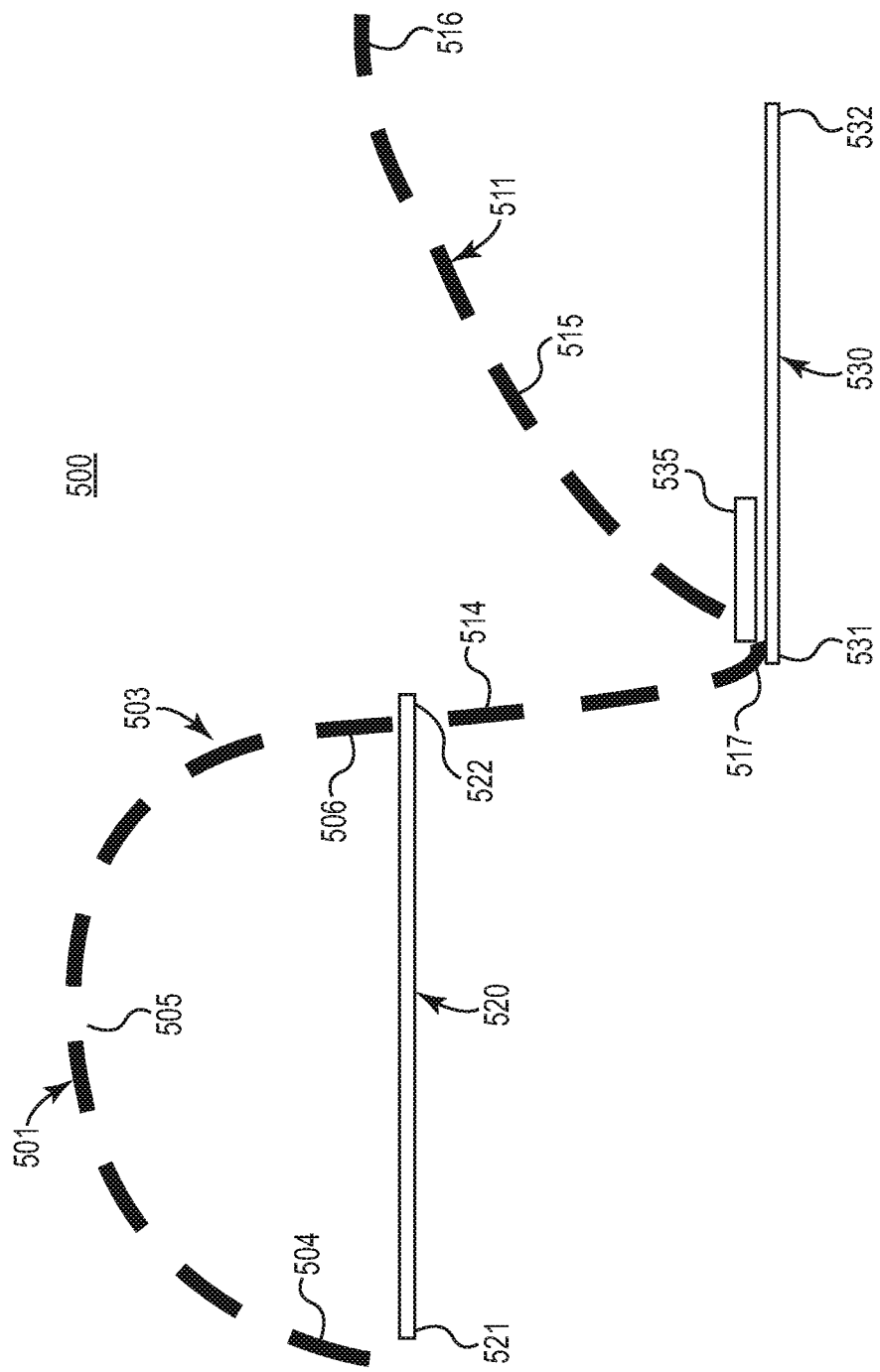

FIG. 9 is a diagram 500 schematically illustrating a method of treating sleep disordered breathing via a stimulation pattern that is modified relative to the stimulation pattern of FIG. 8, according to one embodiment of the present disclosure. As shown in FIG. 9, a respiratory cycle 503 includes an inspiratory phase 501 and an expiratory phase 511. The inspiratory phase 501 includes an initial portion 504, an intermediate portion 505, and an end portion 506 while the expiratory phase 511 includes an initial portion 514, intermediate portion 515, peak 517, and end portion 516. As further shown in diagram 450 of FIG. 9, a shorter duration stimulation burst 535 is applied only in the expiratory phase 511 (for patients having predominantly expiratory-based flow limitations) in addition to the generally continuous pulsed lower amplitude tone stimulation 530. In particular, as shown in FIG. 8, a low amplitude pulsed continuous stimulation (represented by bar 520) is applied in the inspiratory phase 501 and a low amplitude continuous stimulation (represented by bar 530) in the expiratory phase 511. While the additional stimulation burst 535 could be applied anywhere within the expiratory phase 511, in the example shown in FIG. 9, the burst is applied at the initial portion 514 and peak portion 517 of the expiratory phase 511 to ensure full patency during peak expiration. In another aspect, in this arrangement the low level generally continuous stimulation 530 and burst 535 are applied at the point at which the patient has exhibited the most significant flow limitations in the upper airway.

Figure 10:
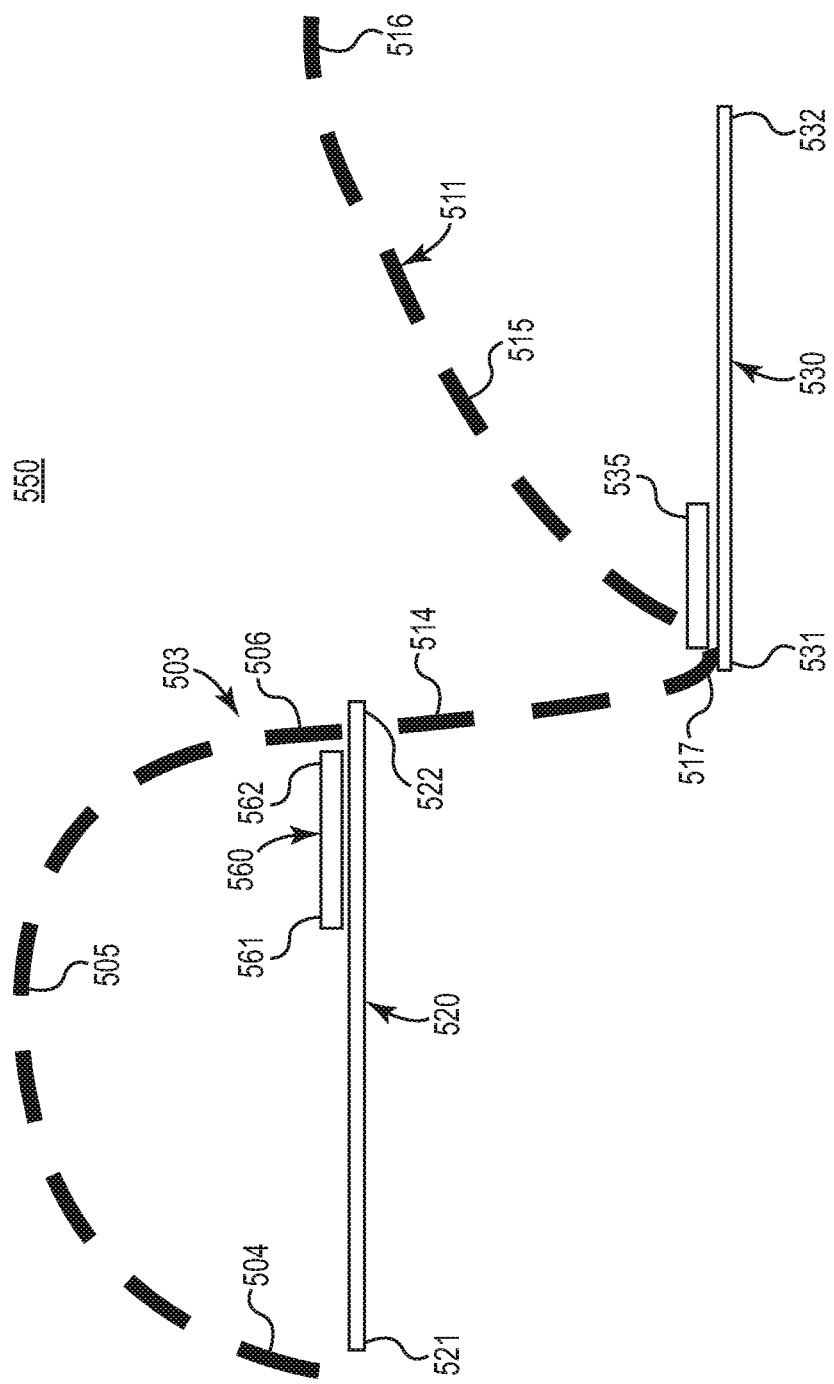

FIG. 10 is a diagram 550 schematically illustrating a method of treating sleep disordered breathing via a stimulation pattern that is modified relative to the stimulation pattern of FIG. 8, according to one embodiment of the present disclosure. As shown in FIG. 10, a respiratory cycle 503 includes an inspiratory phase 501 and an expiratory phase 511. The inspiratory phase 501 includes an initial portion 504, an intermediate portion 505, and an end portion 506 while the expiratory phase 511 includes an initial portion 514, intermediate portion 515, peak 517, and end portion 516.

As further shown in FIG. 10, the stimulation pattern of FIG. 8 is modified so that one additional stimulation burst 560 (in addition to the lower amplitude continuous stimulation 520) is applied at the latter portion of the inspiratory phase 501 and one additional stimulation burst 535 is applied at the initial portion 514 and peak portion 517 of the expiratory phase 511 (in substantially the same manner as in diagram 500 of FIG. 8). In this embodiment, the two bursts 560, 535 of stimulation mimic the stimulation pattern in FIG. 5 with the overall stimulation pattern also including the low level generally continuous stimulation 520, 530 throughout both the inspiratory and expiratory phases 501, 511.

In some embodiments, the moment at which stimulation burst is initiated (within a given inspiratory phase or give expiratory phase) is optimized so that no surplus stimulation is applied. For example, in an example in which a patient has a mixed flow limitation, and a single longer stimulation burst is applied that overlaps both the inspiratory phase and the expiratory phase (such as shown in FIG. 5), an auto-titrating method is applied in which a start point is selected for initiating stimulation during the inspiratory phase and a termination point is selected for terminating stimulation during the expiratory phase.

With further reference to FIGS. 8-10 and 13, it will be understood that adjusting the stimulation amplitude is just one way of modulating the intensity of stimulation, and that in other embodiments, the stimulation intensity is modulated via adjusting the frequency, pulse width, duration, polarity, etc. of pulsed stimulation. For example, instead of applying a stimulation burst of increase amplitude (such as burst 475 in FIG. 8 or burst 535 in FIG. 9), the stimulation burst can include an increased pulse width, increased frequency, or change in polarity.

Figure 11:
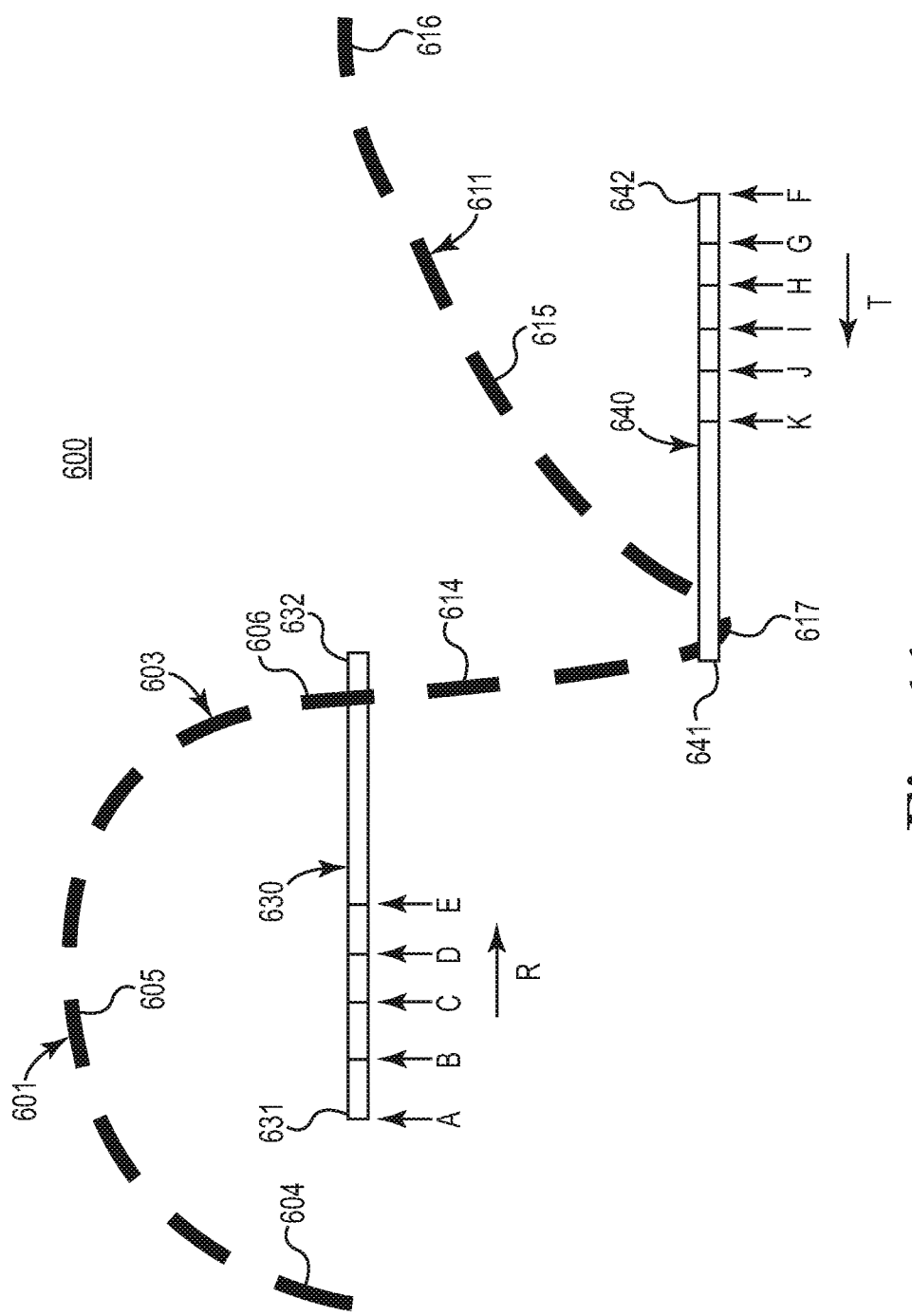

FIG. 11 shows a diagram 600 schematically illustrating a method of treating disordered breathing, according to one embodiment of the present disclosure. As shown in FIG. 11, a respiratory cycle 603 includes an inspiratory phase 601 and an expiratory phase 611. The inspiratory phase 601 includes an initial portion 604, an intermediate portion 605, and an end portion 606 while the expiratory phase 611 includes an initial portion 614, intermediate portion 615, peak 617, and end portion 616. As shown in diagram 600 of FIG. 11, an initial start point for stimulation 630 is identified (point A) and an initial termination point of stimulation 640 is identified (point F). It will be understood that in at least one example, stimulation segments 630,640 are shown as separate elements for illustrative clarity, and that in fact segments 630, 640 represent a single substantially continuous period of stimulation.

Using these parameters, therapy is applied through a period of time to observe whether the applied stimulation is efficacious. In the event that the stimulation period (segments 630 and 640) within the respiratory cycle is sufficient to ameliorate the sleep disordered breathing, the method begins to scale back the total duration of the stimulation period (segments 630, 640). Accordingly, the start point of stimulation segment 630 is moved to point B, corresponding to a shorter period of stimulation (in the inspiratory phase 601), and therapy is applied for a period of many respiratory cycles while observing whether the shortened duration of stimulation is efficacious. This adjustment process is continued in which the duration of stimulation segment 630 in the inspiratory phase 601 is reduced one step at a time (as represented by directional arrow R), until a start point (e.g. A, B, C, D, E, etc.) is identified at which the inspiratory-phase stimulation segment 630 becomes too short as evidenced by the stimulation starting to lose its effectiveness in maintaining and/or restoring airway patency. In other words, the start point is moved in decrements closer to the end portion of the inspiratory phase until a loss of efficacious stimulation therapy is identified.

In one example, once the start point has been adjusted by a decrement (one step), the new duration is maintained for a set of consecutive respiratory cycles to provide a sufficient period of time over which to evaluate the new settings.

With this information, one can identify the last initiation point at which the desired effectiveness was achieved, and this point is adopted as the optimal start point for stimulation segment 630 in the inspiratory phase 610 for this patient. For example, if the start point D resulted in a stimulation segment 630 that proved ineffective in maintaining or restoring airway patency, while start point C was the last successful start point, then the optimal stimulation segment 630 would have a start point C. Once the optimal start point is adopted, each stimulation segment 630 within a give respiratory cycle 603 would begin at start point C.

In one example, the size of the decrements or steps between the respective start points (A, B, C, etc.) correspond to a fraction (such as ⅒, ⅕, or ⅛, etc. of the entire duration of the first portion 360 of the stimulation period 358.

In another example, the initial starting point (e.g. A) is selected to correspond to one of the example durations (two-thirds, one-half, or one-third) of the first portion 360 of the generally continuous stimulation period 358 shown in FIG. 5B.

A similar method is applied to the expiratory phase 611 such that the optimal termination point of the stimulation period (segments 630 and 640) is determined for a given respiratory cycle. In doing so, an initial termination point (e.g. point F) for stimulation segment 640 is identified, and therapy is applied. Provided that efficacy was achieved, the method continues by adopting an earlier termination point (e.g. point G), corresponding to a shorter period of stimulation (in the expiratory phase 611), and therapy is applied for a period of time covering many respiratory cycles. The response of the patient is observed to determine if any loss of efficacy has occurred due to shortening the stimulation segment 640. This process is continued in which the duration of stimulation 640 in the expiratory phase 611 is reduced one step at a time (as represented by directional arrow T), until a termination point (anyone of points F, G, H, I, J, K, etc.) is identified at which the expiratory-phase stimulation 640 becomes too short as evidenced by the stimulation starting to lose its effectiveness in maintaining and/or restoring airway patency. In other words, the termination point is moved in decrements closer to the beginning portion of the expiratory phase until a loss of efficacious stimulation therapy is identified.

With this information, one can identify the last termination point at which the desired effectiveness was achieved, and this point is adopted as the optimal termination point of stimulation segment 640 for this patient to overcome the mixed flow limitation (i.e. a flow limitation that overlaps both the inspiratory and the expiratory phases 601, 611).

In one example, once the termination point has been adjusted by a decrement (one step), the new duration is maintained for a set of consecutive respiratory cycles to provide a sufficient period of time over which to evaluate the new settings.

In one example, the size of the decrements or steps between the respective termination points (F, G, H, etc.) corresponds to a fraction (such as ⅒, ⅕, or ⅛, etc. of the entire duration of the second portion 380 of the stimulation period 358.

In another example, the initial starting point (e.g. F) is selected to correspond to one of the example durations (two-thirds, one-half, or one-third) of the second portion 380 of the generally continuous stimulation period 358 shown in FIG. 5B.

It will be understood, that in addition to optimizing the duration of the stimulation segments 630, 640 shown in association with FIG. 11, one also can optimize for other parameters of the stimulation, such as amplitude, polarity, frequency, pulse width, etc., where an increase or decrease in amplitude, frequency, pulse width, duration, etc. (or change in polarity) can allow a concomitant decrease or increase in the duration of the stimulation.

In some embodiments, an implantable stimulator also can be operated in a first mode which attempts to maintain airway patency (and is therefore prophylactic) or a second mode, which recovers airway patency that has been lost. In the first mode, a stimulation pattern is applied that uses the minimum amount of stimulation required to maintain airway patency, and may include (but is not limited to) one of the stimulation patterns previously described and illustrated in association with FIGS. 1-11. However, in the event that an apnea occurred despite the attempt by the first mode to prevent conditions leading to apnea, the implantable stimulator would switch to a second, "acute" mode of operation, in which the stimulation pattern would become more aggressive in amplitude, frequency, pulse width, and duration of each stimulation burst. The selected duration, amplitude, and frequency would be based on a pre-obstruction respiratory rate. In one embodiment, managing the switch between the first mode and the second mode, as well as managing the stimulation parameters in the second mode, is performed using substantially the same systems and methods, as described in as described and illustrated in PCT Publication WO/2010/059839, entitled A METHOD OF TREATING SLEEP APNEA, published on May 27, 2010, and which is hereby incorporated by reference.

In some embodiments, a flow limitation in the upper airway is detected via respiratory sensors and/or pressure sensors to determine a relative degree of obstruction. These sensors also can be used to determine whether the obstruction is occurring during inspiration, during expiration, or during both. Moreover, because each type of obstruction yields a pressure/impedance pattern that is characteristic of the particular type of obstruction, one can use this sensing information to determine an efficacious stimulation pattern.

Figure 12:
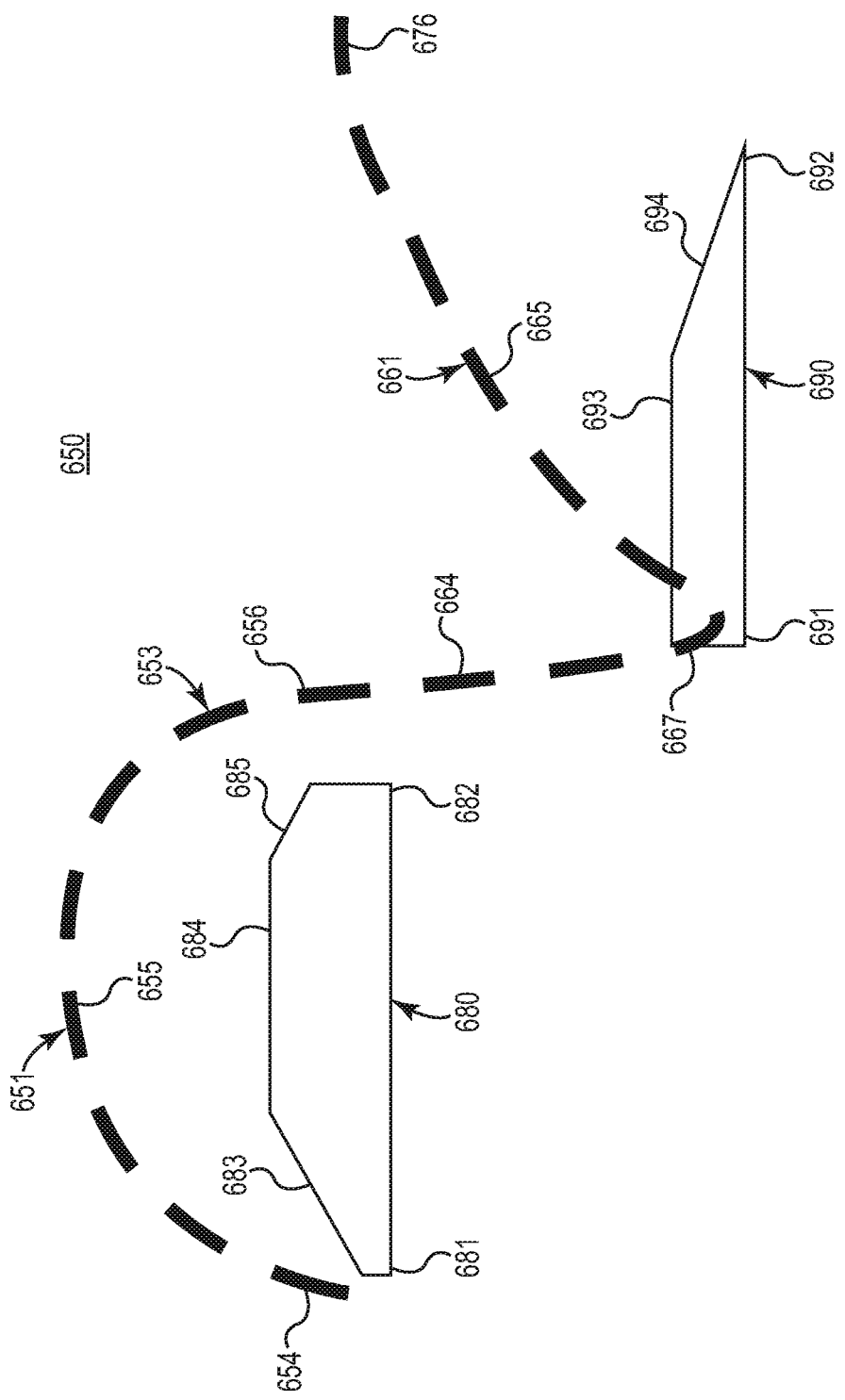

In some embodiments, a stimulation pattern mimics the pattern of the particular breathing phase. As shown in FIG. 12, a respiratory cycle 653 includes an inspiratory phase 651 and an expiratory phase 661. The inspiratory phase 651 includes an initial portion 654, an intermediate portion 655, and an end portion 656 while the expiratory phase 661 includes an initial portion 664, intermediate portion 665, peak 667, and end portion 676. As further shown in the diagram 650 of FIG. 12, stimulation patterns 680 and 690 are applied, in which the greatest volume of stimulation corresponds to ensuring airway patency during the greatest volume of air flow during inspiration and expiration. Accordingly, in one stimulation pattern 680 applied during the inspiratory phase 651, the amplitude of stimulation ramps up through the progression of the inspiratory phase 651. In particular, stimulation pattern 680 includes a start point 681, ramp portion 683, plateau portion 684, descent 685, and end portion 682. In general terms, this ramped stimulation pattern increases the stimulation amplitude (via ramp portion 683) as inspiration commences and then maintains heightened stimulation amplitude (via plateau portion 684) throughout most of the second half of the inspiratory phase 651. While the plateau portion 684 ends prior to completion of the inspiratory phase 651 in the example shown in FIG. 12, it will be understood that the plateau portion 684 could be extended to last through the completion of the inspiratory phase 651.

Meanwhile, in some embodiments, a ramped stimulation pattern 690 is applied to the expiratory phase 661 as further shown in FIG. 12. The stimulation pattern 690 includes a start point 691, plateau portion 693, ramp portion 694, and end portion 692. In general terms, this ramped stimulation pattern begins with a heightened stimulation amplitude (via plateau portion 693) as inspiration commences and then decreases the stimulation amplitude (via ramp portion 694) throughout most of the second half of the expiratory phase 651. In this stimulation pattern 690, a greater stimulation is applied and maintained via plateau portion 693 at (and immediately following) peak expiration 667 in order to ensure airway patency at the beginning of the expiratory phase 661, thereby proactively preventing airway collapse. Once expiration has commenced, then the stimulation is decreased via ramp portion 694, as the volume of air from expiration acts to help maintain airway patency, with the stimulation pattern 690 terminating before the end portion 676 of the expiratory phase 661.

Figure 13:
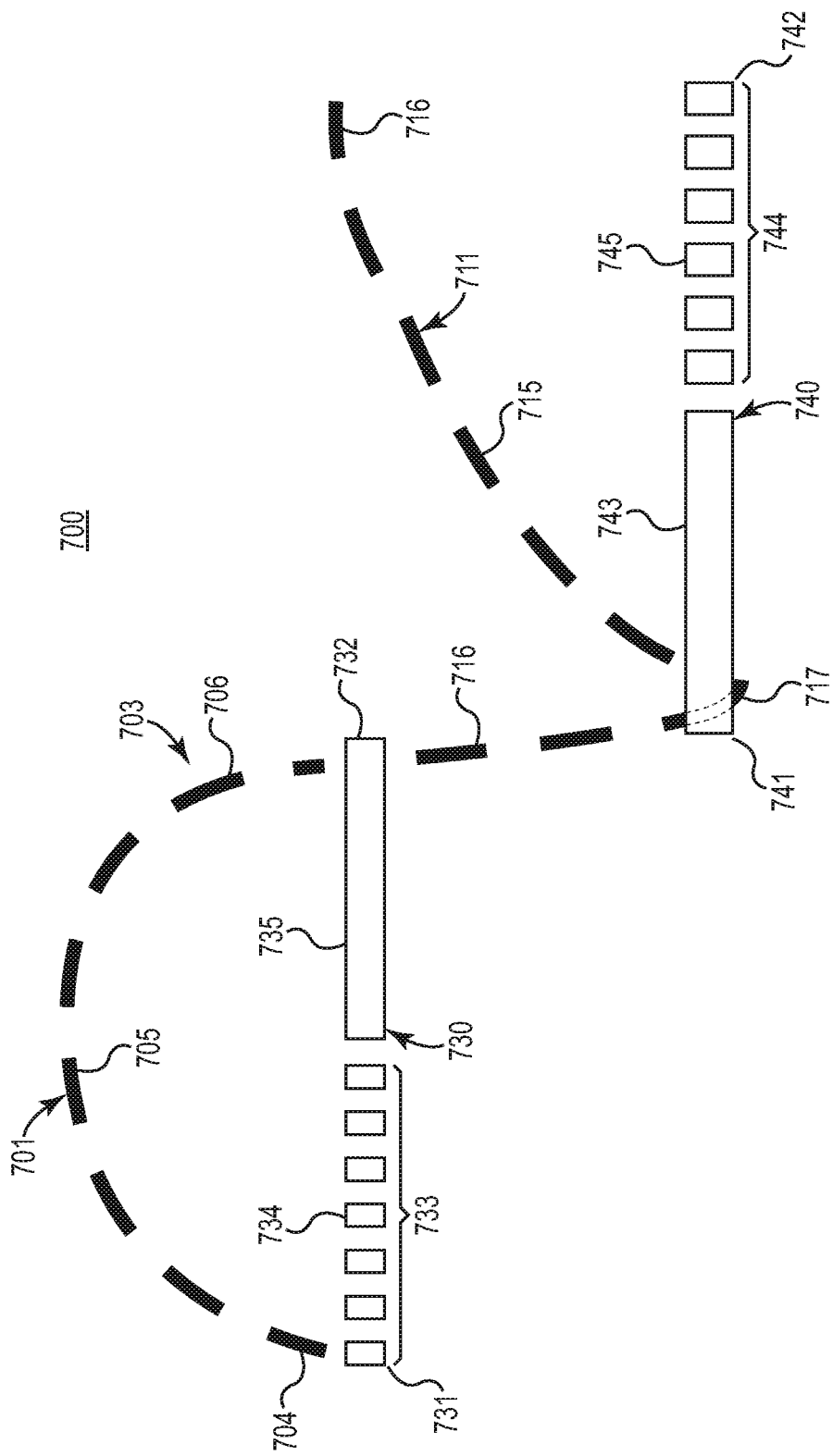

FIG. 13 includes a diagram 700 schematically illustrating a stimulation pattern 730, 740, according to one embodiment of the present disclosure. As shown in FIG. 13, a respiratory cycle 703 includes an inspiratory phase 701 and an expiratory phase 711. The inspiratory phase 701 includes an initial portion 704, an intermediate portion 705, and an end portion 706 while the expiratory phase 711 includes an initial portion 716, intermediate portion 715, peak 717, and end portion 716. As further shown in FIG. 13, the stimulation pattern 730 in the inspiratory phase 701 includes a first portion 733 of bursts 734 of stimulation in the first half of the inspiratory phase 701 and then a generally continuous stimulation segment 735 throughout the second half of the inspiratory phase 701. Meanwhile, the stimulation pattern 740 in the expiratory phase 711 includes a first generally continuous stimulation segment 743 through the first half of the expiratory phase 711 and then a second portion 744 of bursts 745 of stimulation in the second half of the expiratory phase 711. It will be understood that in some embodiments, the stimulation segment 735 and the stimulation segment 743 form a substantially continuous single stimulation segment, but are shown separately in FIG. 13 for illustrative purposes.

In this embodiment, stimulation is applied in bursts 734 in the early portion of the inspiratory phase 701 to maintain tone of the upper airway and then continuous stimulation 735 is applied during the latter half of the inspiratory phase 701 when maximum air flow would occur and just prior to expiration when the airway could be at greater risk for collapse. On the other hand, in the expiratory phase 711, continuous stimulation 743 is applied during the first half of the expiratory phase when there is a greater risk of airway collapse (and maximum air flow needs to take place) while bursts 745 of stimulation are applied during the second half of the expiratory phase 711 to maintain tone and nominal airway patency.

Although specific embodiments have been illustrated and described herein, it will be appreciated by those of ordinary skill in the art that a variety of alternate and/or equivalent implementations may be substituted for the specific embodiments shown and described without departing from the scope of the present disclosure. This application is intended to cover any adaptations or variations of the specific embodiments discussed herein. Therefore, it is intended that this present disclosure be limited only by the claims and the equivalents thereof.

The invention claimed is:

1. A stimulation system comprising:
an implantable pulse generator comprising:
a sensing portion configured to receive sensed respiratory effort information, which includes:
an indication of an upper airway flow limitation when present; and
respiratory cycle information including an inspiratory phase and an expiratory phase; and
a stimulation portion configured to generate and apply a stimulation signal to a hypoglossal nerve via a nerve electrode to increase or maintain patency of an upper airway; and
a controller in communication with at least the sensing element and the stimulation element, wherein the controller comprises a processing resource and a non-transitory computer readable memory storing machine readable instructions, executable via the processing resource, to:
determine an indication of an upper airway flow limitation via the sensed respiratory effort information from the sensing portion, wherein the indicated upper airway flow limitation corresponds to at least a partial obstruction of the upper airway flow associated with obstructive sleep apnea; and
cause, via the sensing portion, stimulation according to a stimulation protocol including stimulation of the hypoglossal nerve to treat the obstructive sleep apnea, the stimulation protocol including application of the stimulation during both of a portion of the inspiratory phase of the respiratory cycle information and a portion of the expiratory phase of the respiratory cycle information.

2. The system of claim 1, wherein the instructions are to implement the stimulation protocol when the indicated upper airway flow limitation predominantly coincides with both of at least an end portion of the inspiratory phase and at least a beginning portion of the expiratory phase but does not predominantly coincide with a beginning portion of the inspiratory phase and with an end portion of the expiratory phase.

3. The system of claim 2, wherein the at least the end portion of the inspiratory phase excludes a beginning portion of the inspiratory phase, and wherein the at least the beginning portion of the expiratory phase excludes an end portion of the expiratory phase.

4. The system of claim 1, wherein the stimulation protocol includes a continuous stimulation period applied during at least a portion of at least some respiratory cycles determined from the received sensed respiratory effort information, wherein the continuous stimulation period predominantly coincides with at least an end portion of the inspiratory phase and with the at least a beginning portion of the expiratory phase, and
wherein the continuous stimulation period includes an initial start point located after a beginning of the inspiratory phase and an initial termination point located prior to an end of the expiratory phase.

5. The system of claim 4, wherein a first portion of the continuous stimulation period coincides with the at least the end portion of the inspiratory phase and has a duration at least one-third of an entirety of the inspiratory phase; and
wherein a second portion of the continuous stimulation period coincides with at least the beginning portion of the expiratory phase and has a duration of at least one-third of the entirety of the expiratory phase.

6. The system of claim 4, wherein the at least the end portion of the inspiratory phase corresponds to at least a majority of the inspiratory phase and the at least the beginning portion of the expiratory phase corresponds to at least a majority of the expiratory phase.

7. The system of claim 1, wherein the stimulation protocol comprises a first stimulation protocol and the instructions are to automatically select between the first stimulation protocol and a third protocol to apply stimulation generally synchronous with the inspiratory phase when the flow limitation generally coincides with the inspiratory phase.

8. The system of claim 1, comprising:
the nerve electrode electrical couplable to the stimulation portion of the pulse generator.

9. The system of claim 7, comprising:
a respiration sensor to sense the respiratory effort information and in communication with the sensing portion of the implantable pulse generator to provide the sensed respiratory effort information to the sensing portion.

10. The stimulation system of claim 1, wherein the instructions are to adjust an intensity of the applied stimulation based on the determined indication of the upper airway flow limitation.

* * * * *